United States Patent [19]
Takaya et al.

[11] 4,366,153
[45] Dec. 28, 1982

[54] CEPHEM COMPOUNDS

[75] Inventors: Takao Takaya, Kawanishi; Takashi Masugi, Toyonaka; Hisashi Takasugi, Osaka; Hiromu Kochi, Sakai, all of Japan

[73] Assignee: Fujisawa Pharmaceutical Co., Ltd., Osaka, Japan

[21] Appl. No.: 123,165

[22] Filed: Feb. 20, 1980

Related U.S. Application Data

[63] Continuation-in-part of Ser. No. 71,302, Aug. 30, 1979, which is a continuation-in-part of Ser. No. 941,660, Sep. 12, 1978, Pat. No. 4,220,761.

[30] Foreign Application Priority Data

Sep. 11, 1978 [GB] United Kingdom ............... 36399/78
Mar. 13, 1979 [GB] United Kingdom ................ 7908799
Mar. 26, 1979 [GB] United Kingdom ................ 7910499

[51] Int. Cl.³ .................. A61K 31/545; C07D 501/56
[52] U.S. Cl. ........................................ 424/246; 544/27
[58] Field of Search ........................... 544/27; 424/246

[56] References Cited
U.S. PATENT DOCUMENTS 4,098,888  7/1978  Ochiai et al. ........................... 544/21
4,220,761  9/1980  Takaya et al. ......................... 544/27
4,278,793  7/1981  Durckheimer et al. ............... 544/27

Primary Examiner—Paul M. Coughlan, Jr.
Attorney, Agent, or Firm—Dayton R. Stemple

[57] ABSTRACT

Bacteriostatic cephem compounds and processes for preparing same having the formula:

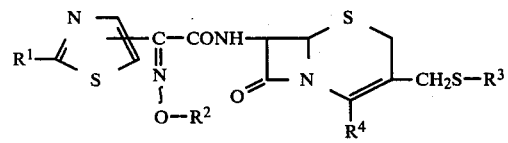

wherein $R^1$ is amino; $R^2$ is optionally substituted alkyl, $C_{3-8}$ cycloalkyl, lower alkenyl, or lower alkynyl; $R^3$ is amino and/or alkyl substituted heterocyclic group; and $R^4$ carboxy.

3 Claims, No Drawings

CEPHEM COMPOUNDS

This is a continuation-in-part application of Ser. No. 71,302, filed Aug. 30, 1979, which in turn is a continuation-in-part application of Ser. No. 941,660, filed Sept. 12, 1978, now U.S. Pat. No. 4,220,761.

This invention relates to new cephem compound. More particularly, it relates to new 3,7-disubstituted-3-cephem-4-carboxylic acid and its pharmaceutically acceptable salt, which have antimicrobial activities, and processes for preparation thereof, to pharmaceutical composition comprising the same and method of using the same prophylactically and a therapeutically for treatment of infectious diseases in human being and animals.

Accordingly, the objects of this invention are to provide: new 3,7-disubstituted-3-cephem-4-carboxylic acid and its pharmaceutically acceptable salt, which exhibit excellent antimicrobial activities against a wide variety of pathogenic microorganisms including Gram negative and Gram positive bacteria, processes for preparation of the same, pharmaceutical composition comprising one of the same as an active ingredient, and a method of using the same prophylactically and therapeutically for treatment of infectious diseases caused by pathogenic microorganisms in human being and animals.

The cephem compound provided by this invention can be represented by the formula (I):

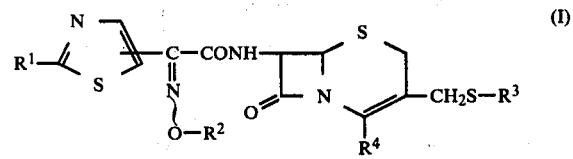

wherein
$R^1$ is amino or protected amino,
$R^2$ is lower alkyl, amino-(lower)-alkyl, protected amino-(lower)-alkyl, hydroxy-(lower)-alkyl, protected hydroxy-(lower)-alkyl, lower alkylthio-(lower)-alkyl, carboxy-(lower)-alkyl, esterified carboxy-(lower)-alkyl, ($C_3$ to $C_8$) cycloalkyl, lower alkenyl or lower alkynyl,
$R^3$ is a heterocylic group substituted with amino(lower)alkyl, protected amino(lower)alkyl, hydroxy(lower)alkyl or both amino and lower alkyl,
$R^4$ carboxy or protected carboxy, provided that $R^3$ is a heterocyclic group substituted with hydroxy(lower)alkyl or both amino and lower alkyl, when $R^2$ is lower alkyl,
and its pharmaceutically acceptable salt.

The compound (I) of this invention can be prepared by processes as shown in the following scheme.

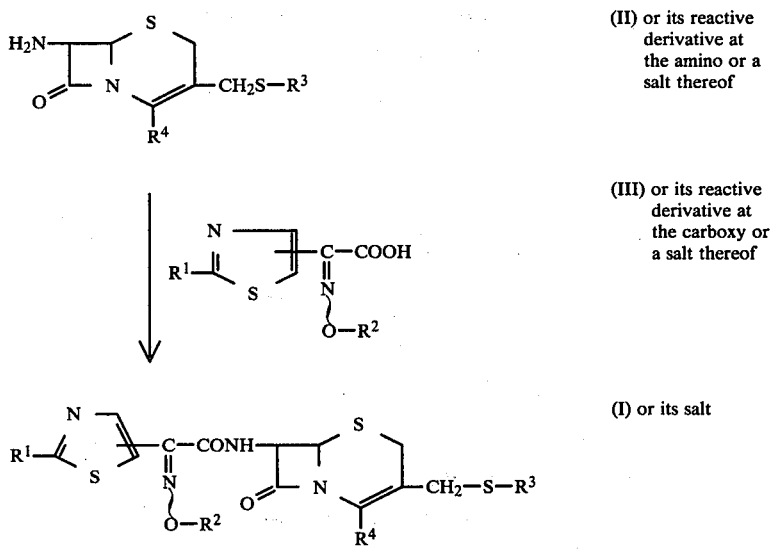

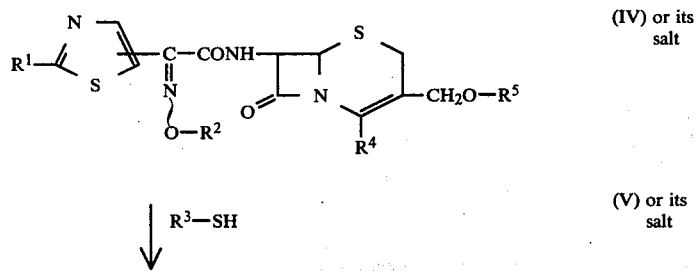

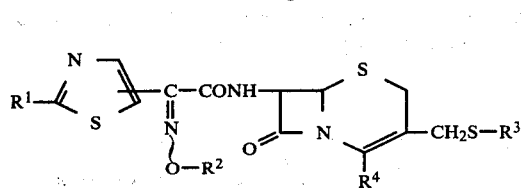 (I) or its salt
Process C: Elimination of amino-protective group in $R_a^1$
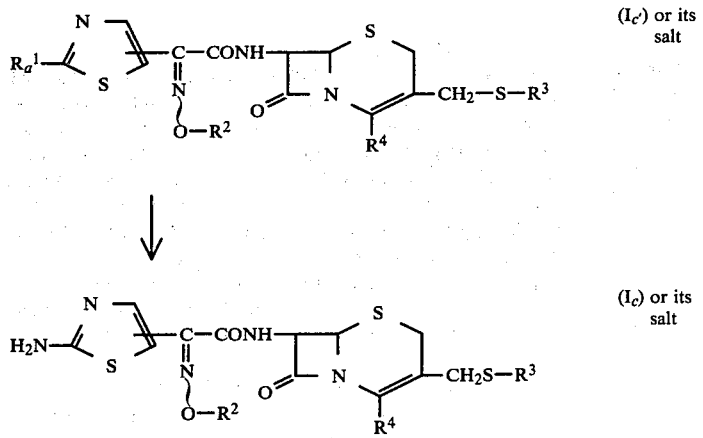
Process D: Elimination of amino-protective group in $R_a^3$
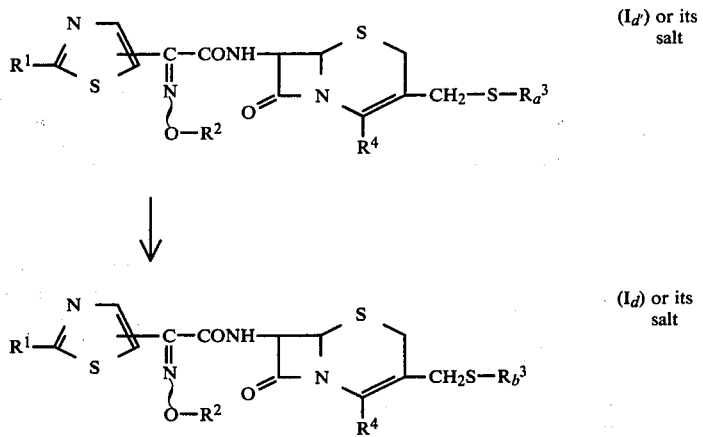
Process E: Elimination of hydroxy-protective group in $R_a^2$
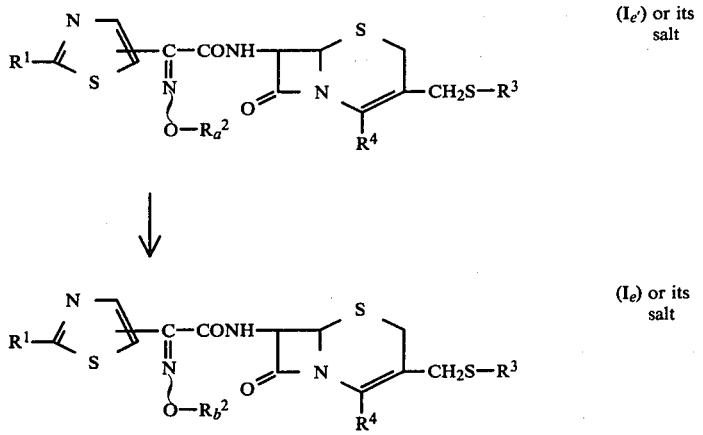
Process F: Elimination of amino-protective group in $R_c^2$

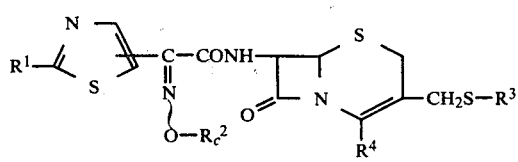 (If) or its salt

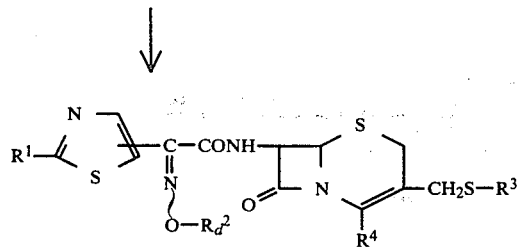 (If) or its salt

Process G: Carboxy formation in $R_e^2$

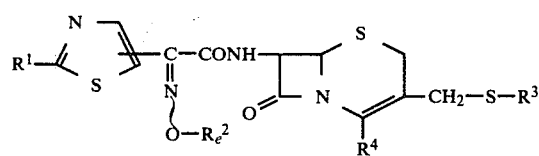 (Ig') or its salt

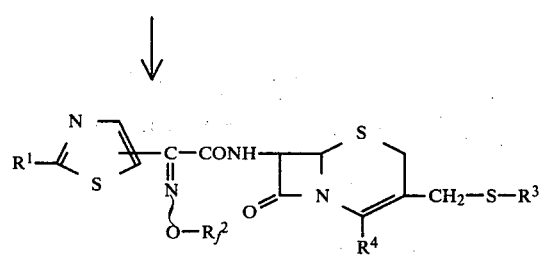 (Ig) or its salt

Process H: Carboxy formation

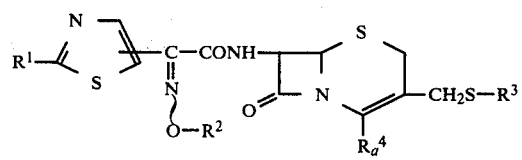 (Ih') or its salt

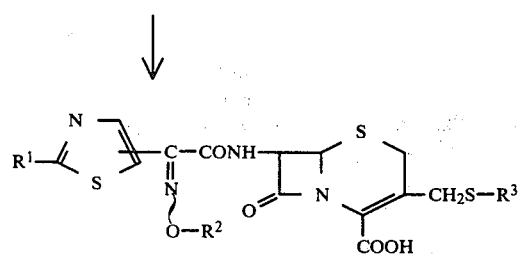 (Ih) or its salt wherein
$R^1$, $R^2$, $R^3$ and $R^4$ are each as defined above,
$R_a^1$ is protected amino,
$R_a^2$ is protected hydroxy(lower)alkyl,
$R_b^2$ is hydroxy(lower)alkyl,
$R_c^2$ is protected amino(lower)alkyl,
$R_d^2$ is amino(lower)alkyl,
$R_e^2$ is esterified carboxy(lower)alkyl,
$R_f^2$ is carboxy(lower)alkyl,
$R_a^3$ is heterocyclic group substituted with protected amino(lower)alkyl,
$R_b^3$ is heterocyclic group substituted with amino(-lower)alkyl,
$R_a^4$ is protected carboxy, and
$R^5$ is acyl.

Among the starting compound in the present invention, some of the starting compound (III) used in Process A are novel and can be represented by the following formula:

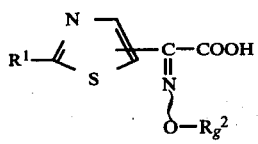

(IIIa)

wherein
R[1] is amino or protected amino, and
$R_g^2$ is amino(lower)alkyl, lower alkoxycarbonylamino(lower)alkyl, hydroxy(lower)alkyl, protected hydroxy(lower)alkyl, lower alkylthio(lower)alkyl, carboxy(lower)alkyl, esterified carboxy(lower)alkyl, ($C_3$ to $C_8$) cycloalkyl or lower alkynyl,
and its ester and a salt thereof.

The starting compound (IIIa) can be prepared by the methods illustrated below.

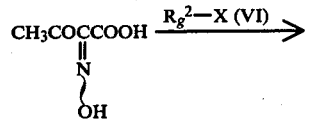

(1)

(Va)
or its ester
or a salt
thereof

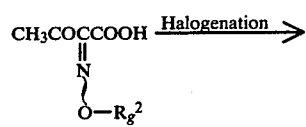

(Vb)
or its ester
or a salt
thereof

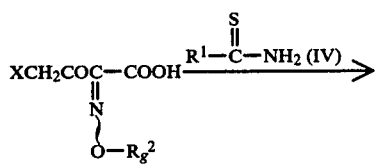

(Vc)
or its ester
or a salt
thereof (III'a)
or its ester
or a salt
thereof

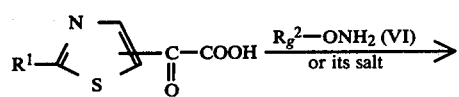

(2)

(Vd)
or its ester or
a salt thereof

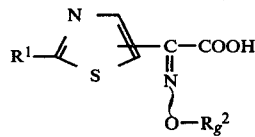

(IIIa)
or its ester or
a salt thereof

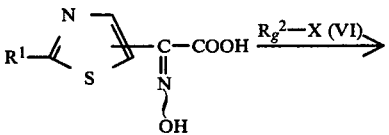

(3)

(Ve)
or its ester or
a salt thereof

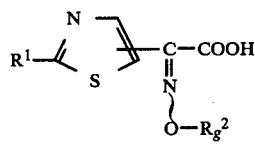

(IIIa)
or its ester or
a salt thereof

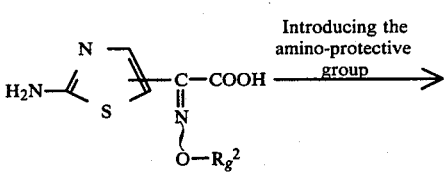

(4)

(IIIb)
or its ester or
a salt thereof

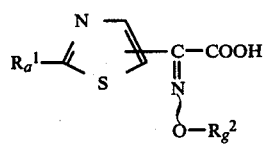

(IIIc)
or its ester or
a salt thereof

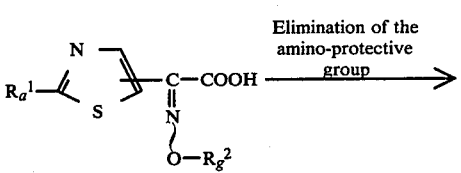

(5)

(IIIc)
or its ester or
a salt thereof

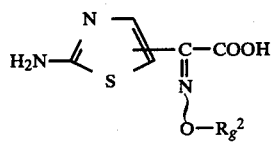

(IIIb)
or its ester or
a salt thereof

-continued

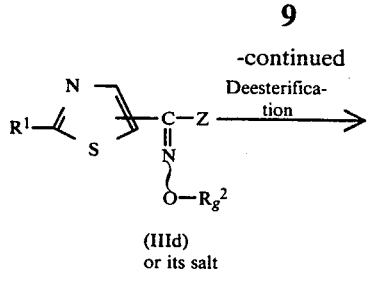

(IIId) or its salt

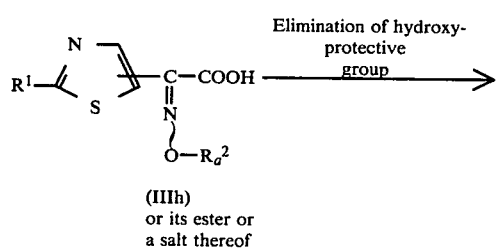

(IIIe) or its salt

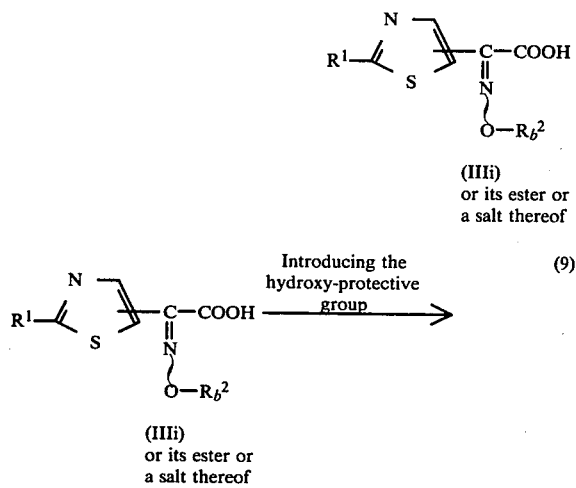

(IIIf) or its ester or a salt thereof (IIIg) or its ester or a salt thereof (IIIh) or its ester or a salt thereof (IIIi) or its ester or a salt thereof -continued

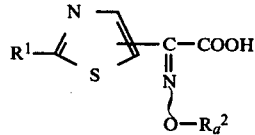

(IIIh) or its ester or a salt thereof

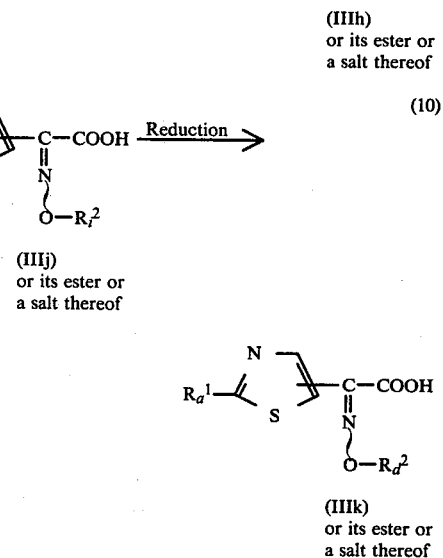

(IIIj) or its ester or a salt thereof (IIIk) or its ester or a salt thereof where
$R^1$, $R_a^1$, $R_a^2$, $R_b^2$, $R_d^2$ and $R_g^2$ are each as defined above,
$R_h^2$ is lower alkoxycarbonylamino(lower)alkyl
$R_i^2$ is azido(lower)alkyl,
X is halogen, and
Z is esterified carboxy.

The terms and definitions described in this specification are illustrated as follows.

(a) Partial structure of the formula:

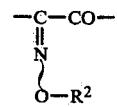

is intended to mean both of the geometric formulae:

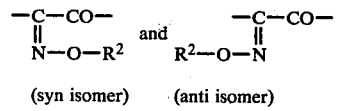

(syn isomer)   (anti isomer)

From the view point of structure-activity relationship, it is to be noted that a syn isomer of the compound (I) tends to be of much higher antimicrobial activity than the corresponding anti isomer, and accordingly the syn isomer of the compound (I) is more preferable antimicrobial agent than the corresponding anti isomer in the prophylactic and therapeutic value.

(b) The thiazolyl group of the formula:

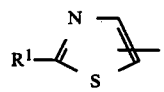

(wherein R[1] is as defined above) is well known to lie in tautomeric relation with a thiazolinyl group, and the tautomerism between the said thiazolyl and thiazolinyl groups can be illustrated by the following equilibrium:

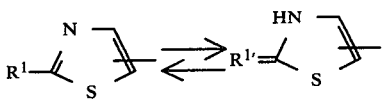

(wherein
R[1] is as defined above, and
R[1'] is imino or protected imino)

Accordingly, it is to be understood that both of the said groups are substantially the same, and the tautomers consisting of such groups are regarded as the same compounds. Therefore, both of the tautomeric forms of the compounds having such groups in their molecule are included in the scope of this invention and designated inclusively with one expression "thiazolyl" and represented by the formula:

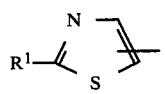

(wherein R[1] is as defined above) only for the convenient sake throughout this specification.

In the above and subsequent descriptions of this specification, suitable examples and illustration of the various definitions which this invention intends to include within the scope thereof are explained in detail as follows.

The term "lower" is used to intend a group having 1 to 6 carbon atom(s), unless otherwise provided.

The term "protective group" in the terms "protected amino" and "protected amino(lower)alkyl" may include a conventional N-protective group such as acyl, substituted or unsubstituted ar(lower)-alkyl (e.g. benzyl, benzhydryl, trityl, 4-methoxybenzyl, 3,4-dimethoxybenzyl, etc.), halo(lower)alkyl (e.g. trichloromethyl, trichloroethyl, trifluoromethyl, etc.), tetrahydropyranyl, substituted phenylthio, substituted alkylidene, substituted aralkylidene, substituted cycloalkylidene, or the like.

Suitable acyl for the N-protective group may be aliphatic acyl group and acyl group containing an aromatic or heterocyclic ring. And, suitable examples of the said acyl may be lower alkanoyl (e.g., formyl, acetyl, propionyl, butyryl, isobutyryl, valeryl, isovaleryl, oxalyl, succinyl, pivaloyl, etc.), preferably one having 1 to 4 carbon atom(s), more preferably one having 1 to 2 carbon atom(s); lower alkoxycarbonyl having 2 to 7 carbon atoms (e.g., methoxycarbonyl, ethoxycarbonyl, propoxycarbonyl, 1-cyclopropylethoxycarbonyl, isopropoxycarbonyl, butoxycarbonyl, t-butoxycarbonyl, pentyloxycarbonyl, t-pentyloxycarbonyl, hexyloxycarbonyl, etc.), preferably one having 2 to 6 carbon atoms; lower alkanesulfonyl (e.g., mesyl, ethanesulfonyl, propanesulfonyl, isopropanesulfonyl, butanesulfonyl, etc.);

arenesulfonyl (e.g., benzenesulfonyl, tosyl, etc.); aroyl (e.g., benzoyl, toluoyl, naphthoyl, phthaloyl, indancarbonyl, etc.); ar(lower)alkanoyl (e.g., phenylacetyl, phenylpropionyl, etc.);

ar(lower)alkoxycarbonyl (e.g., benzyloxycarbonyl, phenethyloxycarbonyl, etc.); and the like.

The acyl as stated above may have 1 to 3 suitable substituent(s) such as halogen (e.g., chlorine, bromine, iodine or fluorine), hydroxy, cyano, nitro, lower alkoxy (e.g., methoxy, ethoxy, propoxy, isopropoxy, etc.), lower alkyl (e.g., methyl, ethyl, propyl, isopropyl, butyl, etc.), lower alkenyl (e.g., vinyl, allyl, etc.), aryl (e.g., phenyl, tolyl, etc.), or the like, and preferable example is mono(or di or tri)halo(lower)alkanoyl (e.g., chloroacetyl, dichloroacetyl, trifluoroacetyl, etc.).

And further, the reaction product of a silan, boron, aluminium or phosphorus compound with the amino group may also be included in the N-protective group. Suitable examples of such compounds may be trimethylsilyl chloride, trimethoxysilyl chloride, boron trichloride, butoxyboron dichloride, aluminum trichloride, diethoxy aluminum chloride, phosphorus dibromide, phenylphosphorus dibromide, or the like.

The term "lower alkyl" and "lower alkyl moiety" in the terms "amino(lower)alkyl", "protected amino(lower)alkyl", "hydroxy(lower)alkyl", "protected hydroxy(lower)alkyl", "lower alkylthio(lower)alkyl", "carboxy(lower)alkyl", "esterified carboxy(lower)alkyl" and "lower alkoxycarbonylamino(lower)alkyl" may include a residue of straight and branched alkane having 1 to 6 carbon atom(s) such as methyl, ethyl, propyl, isopropyl, butyl, isobutyl, t-butyl, pentyl, neopentyl, hexyl and the like, and preferably the one having 1 to 4 carbon atom(s).

The term "protective group" in the term "protected hydroxy(lower)alkyl" may include a conventional O-protective group such as acyl as aforementioned, or the like.

The term "(C$_3$ to C$_8$)cycloalkyl" may include cyclopropyl, cyclopentyl, cyclohexyl, cycloheptyl and the like, and preferably (C$_5$ to C$_6$)cycloalkyl.

The term "lower alkenyl" may include a residue of a straight or branched alkene having 2 to 6 carbon atoms, such as vinyl, allyl, 1-propenyl, isopropenyl, butenyl, isobutenyl, pentenyl, hexenyl and the like, and preferably the ones having up to 5 carbon atoms.

The term "lower alkynyl" may include a residue of a straight or branched alkyne having 2 to 6 carbon atoms, such as ethynyl, propargyl, 1-propynyl, 3-butynyl, 2-butynyl, 4-pentynyl, 3-pentynyl, 2-pentynyl, 1-pentynyl, 5-hexynyl and the like, and preferably the ones having up to 5 carbon atoms.

The term "heterocyclic group" in the term "a heterocyclic group substituted with amino(lower)alkyl, protected amino(lower)alkyl, hydroxy(lower)alkyl or both amino and lower alkyl" may include unsaturated 5 to 6-membered heterocyclic group containing at least one hetero atom selected from oxygen, sulfur and nitrogen atoms.

And, preferable heterocyclic group may be the one such as unsaturated 5 to 6-membered heterocyclic group containing 1 to 2 oxygen atom(s), for example, furyl;

unsaturated 5 to 6-membered heterocyclic group containing 1 to 4 nitrogen atom(s), for example, pyrrolyl, imidazolyl, pyrazolyl, pyridyl, picolyl, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

unsaturated 5 to 6-membered heterocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

unsaturated 5 to 6-membered heterocyclic group containing 1 to 2 sulfur atom(s) and 1 to 3 nitrogen atom(s), for example, thiazolyl, isothiazolyl, thiadiazolyl (e.g., 1,2,4-thiadiazolyl, 1,3,4-thiadiazolyl, 1,2,5-thiadiazolyl, etc.), etc.; and the like.

The term "protected carboxy" may include esterified carboxy, amidated carboxy or the like.

Suitable examples of "the ester" and "ester moiety" in the "esterified carboxy" may be lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.);

lower alkenyl ester (e.g., vinyl ester, allyl ester, etc.);

lower alkynyl ester (e.g., ethynyl ester, propynyl ester, etc.);

lower alkoxy(lower)alkyl ester (e.g., methoxymethyl ester, ethoxymethyl ester, isopropoxymethyl ester, 1-methoxyethyl ester, 1-ethoxyethyl ester, etc.);

lower alkylthio(lower)alkyl ester (e.g., methylthiomethyl ester, ethylthiomethyl ester, ethylthioethyl ester, isopropylthiomethyl ester, etc.);

halo(lower)alkyl ester (e.g., 2-iodoethyl ester, 2,2,2-trichloroethyl ester, etc.);

lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);

lower alkanesulfonyl(lower)alkyl ester (e.g., mesylmethyl ester, 2-mesylethyl ester, etc.);

ar(lower)alkyl, for example, phenyl(lower)alkyl ester which may have one or more suitable substituent(s) (e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.);

aryl ester which may have one or more suitable substituent(s) (e.g., phenyl ester, tolyl ester, t-butylphenyl ester, xylyl ester, mesityl ester, cumenyl ester, salicyl ester, etc.); an ester with a silyl compound such as tri(lower)alkylsilyl compound, di(lower)alkylalkoxysilyl compound or tri(lower)alkoxysilyl compound, for example, tri(lower)alkylsilyl ester (e.g., trimethyl silyl ester, triethylsilyl ester, etc.), di(lower)alkylalkoxy silyl ester (e.g., dimethylmethoxysilyl ester, dimethylethoxysilyl ester, diethylmethoxysilyl ester, etc.) or tri(lower)alkoxysilyl ester (e.g., trimethoxysilyl ester, triethoxysilyl ester, etc.), or the like.

More particularly, the preferable example of ester may be nitrophenyl(lower)alkyl ester ester (e.g., 4-nitrobenzyl ester, 4-nitrophenethyl ester, etc.), lower alkyl ester (e.g., methyl ester, ethyl ester, propyl ester, isopropyl ester, butyl ester, isobutyl ester, tert-butyl ester, pentyl ester, neopentyl ester, hexyl ester, etc.).

The term "esterified carboxy moiety" in the term "esterified carboxy(lower)alkyl" may be referred to the aforementioned examples of esterified carboxy.

More particularly, the preferable examples of $R^1$ to $R^4$ are illustrated as follows.

The preferable examples of $R^1$ may be amino or acylamino [more preferably, lower alkanoylamino (e.g., formamido, acetamido, etc.) or trihalo(lower)alkanoylamino (e.g., trifluoroacetamido, etc.)].

The preferable examples of $R^2$ may be lower alkyl (e.g., methyl, ethyl, propyl, isopropyl, butyl, isobutyl, pentyl, hexyl, etc.), amino(lower)alkyl (e.g., aminomethyl, aminoethyl, aminopropyl, etc.), acylamino(lower)alkyl [more preferably, lower alkoxycarbonylamino(lower)alkyl (e.g., methoxycarbonylaminomethyl, ethoxycarbonylaminoethyl, propoxycarbonylaminopropyl, t-butoxycarbonylaminoethyl, t-butoxycarbonylaminopropyl, etc.)], hydroxy(lower)alkyl (e.g., hydroxymethyl, hydroxyethyl, hydroxypropyl, etc.), acyloxy(lower)alkyl [more preferable, lower alkanoyloxy(lower)alkyl (e.g., formyloxymethyl, formyloxyethyl, acetoxyethyl, formyloxypropyl, etc.)], lower alkylthio(lower)alkyl (e.g., methylthiomethyl, methylthioethyl, ethylthioethyl, etc.), carboxy(lower)alkyl (e.g., carboxymethyl, carboxypropyl, etc.), esterified carboxy(lower)alkyl [more preferably, lower alkoxycarbonyl(lower)alkyl (e.g., methoxycarbonylmethyl, ethoxycarbonylmethyl, t-butoxycarbonylmethyl, propoxycarbonylethyl, etc.(], ($C_3$ to $C_8$)cycloalkyl [more preferably, ($C_5$ to $C_6$)cycloalkyl (e.g., cyclopentyl, cyclohexyl, etc.)], lower alkenyl (e.g., vinyl, allyl, etc.) or lower alkynyl (e.g., ethynyl, propargyl, etc.).

The preferable examples of $R^3$ may be unsaturated 5 to 6-membered heterocyclic group containing 1 to 4 nitrogen atom(s) substituted with amino(lower)alkyl, lower alkoxycarbonylamino(lower)-alkyl, hydroxy(lower)alkyl or both amino and lower alkyl [more preferably, amino(lower)alkyltetrazolyl (e.g., 1-aminomethyl-1H-tetrazol-5-yl, 1-(2-aminoethyl)-1H-tetrazol-5-yl, 1-(3-aminopropyl)-1H-tetrazol-5-yl, etc.), lower alkoxycarbonylamino(lower)alkyl-tetrazolyl (e.g., 1-methoxycarbonylaminomethyl-1H-tetrazol-5-yl, 1-(2-t-butoxycarbonylaminoethyl)-1H-tetrazol-5-yl, 1-(3-t-butoxycarbonylaminopropyl)-1H-tetrazol-5-yl, etc.), hydroxy(lower)alkyltetrazolyl (e.g., 1-hydroxymethyl-1H-tetrazol-5-yl, 1-(2-hydroxyethyl)-1H-tetrazol-5-yl, 1-(3-hydroxypropyl)-1H-tetrazol-5-yl, etc.) or triazolyl substituted with both amino and lower alkyl (e.g., 4-amino-5-methyl-4H-1,2,4-triazol-3-yl, 4-amino-5-ethyl-4H-1,2,4-triazol-3-yl, etc.)] or unsaturated 5 to 6-membered heterocyclic group containing 1 to 2 sulfur atom(s) and 1 to 3 nitrogen atom(s) substituted with amino(lower)alkyl or lower alkoxycarbonylamino(lower)alkyl [more preferably, amino(lower)alkylthiadiazolyl (e.g., 5-aminomethyl-1,3,4-thiadiazol-2-yl, 5-(2-aminoethyl)-1,3,4-thiadiazol-2-yl, etc.) or lower alkoxycarbonylamino(lower)alkyl-thiadiazolyl (e.g. 5-methoxycarbonylaminomethyl-1,3,4-thiadiazol-2-yl, 5-t-butoxycarbonyl-aminomethyl-1,3,4-thiadiazol-2-yl, 5-(2-t-butoxycarbonylaminoethyl)-1,3,4-thiadiazol-2-yl, etc.)].

The preferable example of $R^4$ may be carboxy.

Suitable "pharmaceutically acceptable salt" of the compound (I) includes a conventional non-toxic salt, and may be a salt with an inorganic base or acid, for example, a metal salt such as an alkali metal salt (e.g. sodium salt, potassium salt, etc.) and an alkaline earth metal salt (e.g. calcium salt, magnesium salt, etc.), ammonium salt, an inorganic acid salt (e.g. hydrochloride, hydrobromide, sulfate, phosphate, carbonate, bicarbonate, etc.), a salt with an organic base or acid, for example, an amine salt (e.g. trimethylamine salt, triethylamine salt, pyridine salt, procaine salt, picoline salt, dicyclohexylamine salt, N,N'-dibenzylethylenediamine salt, N-methylglucamine salt, diethanolamine salt, triethanolamine salt, tris(hydroxymethylamino)methane salt, phenethylbenzylamine salt, etc.), an organic carboxylic or sulfonic acid salt (e.g. acetate, maleate, lactate, tartrate, mesylate, benzenesulfonate, tosylate, etc.), a basic or acidic amino acid salt (e.g. arginine salt, aspartic acid salt, glutamic acid salt, lysine salt, serine salt, etc.) and the like.

The processes for preparing the object compounds (I) of the present invention are explained in details in the following.

Process A

N-Acylation

A compound (I) or its salt can be prepared by reacting a compound (II) or its reactive derivative at the amino or a salt thereof with a compound (III) or its reactive derivative at the carboxy or a salt thereof according to a conventional manner of so-called amidation reaction well known in β-lactam chemistry.

Suitable reactive derivative at the amino group of the compound (II) may include a conventional reactive derivative as used in a wide variety of amidation reaction, for example, isocyanato, isothiocyanato, a derivative formed by the reaction of a compound (II) with a silyl compound (e.g. trimethylsilylacetamide, bis(trimethylsilyl)acetamide, etc.), with an aldehyde compound (e.g. acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde, etc., or the corresponding hydrate, acetal, hemiacetal or enolate thereof), with a ketone compound (e.g. acetone, methyl ethyl ketone, methyl isobutyl ketone, acetylacetone, ethyl acetoacetate, etc., or the corresponding ketal, hemiketal or enolate thereof), with phosphorus compound (e.g. phosphorus oxychloride, phosphorus chloride, etc.), or with a sulfur compound (e.g. thionyl chloride, etc.), and the like.

Suitable salt of the compound (II) may be referred to those as exemplified for the compound (I).

Suitable reactive derivative at the carboxy group of the compound (III) may include, for example, an acid halide, an acid anhydride, an activated amide, an activated ester, and the like, and preferably acid halide such as acid chloride, acid bromide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.); a symmetrical acid hydride; an activated acid amide with imidazole, 4-substituted imidazole, dimethylpyrazole, triazole or tetrazole; an activated ester (e.g. cyanomethyl ester, methoxymethyl ester, dimethylaminomethyl ester, vinyl ester, propargyl ester, p-nitrophenyl ester, 2,4-dinitrophenyl ester, trichlorophenyl ester, pentachlorphenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

Suitable salt of the compound (III) may include a salt with an inorganic base such as alkali metal salt (e.g. sodium salt, potassium salt, etc.) and an alkaline earth metal salt (e.g. calcium salt, magnesium salt, etc.) a salt with an organic base such as tertiary amine (e.g. trimethylamine salt, triethyl-amine salt, N,N-dimethylaniline salt, pyridine salt, etc.), a salt with an inorganic acid (e.g. hydro-chloride, hydrobromide, etc.) and the like.

The suitable reactive derivatives of the compounds (II) and (III) can optionally be selected from the above according to the kind of the compounds (II) and (III) to be used practically, and to the reaction conditions.

The reaction is usually carried out in a conventional solvent such as water, acetone, dioxane, acetonitrile, chloroform, benzene, methylene chloride, ethylene chloride, tetrahydrofuran, ethyl acetate, N,N-dimethylformamide, pyridine or any other solvent which does not adversely influence the reaction, or an optional mixture thereof.

When the acylating agent (III) is used in a form of free acid or salt in this reaction, the reaction is preferably carried out in the presence of a condensing agent such as a carbodiimide compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), a bisimidazolide compound (e.g. N,N'-carbonylbis(2-methylimidazole), etc.), an imine compound (e.g. pentamethyleneketene-N-cyclohexylimine, diphenylketene-N-cyclohexylimine, etc.), an olefinic or acetylenic ether compound (e.g. ethoxyacetylene, β-chlorovinylethyl ether, etc.), 1-(4-chlorobenzenesulfonyloxy)-6-chloro-1H-benzotriazole, N-ethylbenzisoxazolium salt, N-ethyl-5-phenylisoxazolium-3'-sulfonate, a phosphorus compound (e.g. polyphosphoric acid, trialkyl phosphite, ethyl polyphosphate, isopropyl polyphosphate, phosphorus oxychloride, phosphorus trichloride, diethylchlorophosphite, orthophenylene chlorophosphite, etc.), thionyl chloride, oxalyl chloride, Vilsmeier reagent prepared by the reaction of dimethylformamide with thionyl chloride, phosphoryl chloride, phosgene or the like.

The reaction temperature is not critical, and the reaction is usually carried out under cooling or at ambient temperature.

In order to obtain a syn isomer of the compound (I) selectively and in high yield, it is preferable to use a syn isomer of the acylating agent (III), and to conduct the reaction under a selected reaction condition. That is, a syn isomer of the compound (I) can be obtained selectively and in high yield by conducting the reaction of a compound (II) with a syn isomer of the acylating agent (III), for example, in the presence of a Vilsmeier reagent as mentioned above and under around neutral condition.

The object compound (I) and its salt are useful as an antimicrobial agent, and a part thereof can also be used as a starting material in the other processes as explained below.

Process B

Thioetherification

A compound (I) or its salt can be prepared by reacting a compound (IV) or its salt with a thiol compound (V) or its salt.

"Acyl" group for $R^5$ of the starting compound (IV) may be lower alkanoyl having 2 to 6 carbon atom(s) (e.g. acetyl, propionyl, etc.), aroyl (e.g. benzoyl, toluoyl, etc.) or the like.

Suitable salt of the compound (IV) may be referred to those as exemplified for the compound (I).

Suitable salt of the thiol compound (V) may include a metal salt such as alkali metal salt (e.g. sodium salt, potassium salt, etc.), and acid salt such as hydrohalide (e.g. hydrochloride, hydrobromide, etc.) or the like.

This reaction may be carried out in a solvent such as water, acetone, chloroform, nitrobenzene, methylene chloride, ethylene chloride, dimethylformamide, methanol, ethanol, diethyl ether, tetrahydrofuran, dimethylsulfoxide, buffer solution or any other solvent which does not adversely affect the reaction, preferably in ones having strong polarities. Among the solvents, hydrophilic solvents may be used in a mixture with water. The reaction is preferably conducted in weekly basic or around neutral condition. When the compound (IV) and/or the thiol compound (V) is used in a free form, the reaction is preferably conducted in the presence of a base, for example, inorganic base such as alkali metal hydroxide, alkali metal carbonate, alkali metal bicarbonate, organic base such as trialkylamine, pyridine, and the like. The reaction temperature is not critical, and the reaction is usually carried out at ambient temperature or under warming.

Process C

Elimination of amino-protective group in $R_a^1$

A compound ($I_c$) or its salt can be prepared by subjecting a compound ($I_{c'}$) or its salt to elimination reaction of the protective group in the protected amino for $R_a^1$.

The elimination reaction may be conducted in accordance with a conventional method such as hydrolysis, reduction or the like. These methods may be selected according to the kind of the protective group to be eliminated.

The hydrolysis may include a method using an acid (acidic hydrolysis), a base (basic hydrolysis) or hydrazine, and the like. Among these methods, acidic hydrolysis is one of the common and preferable methods for eliminating the protective group such as an acyl lower alkanoyl (e.g. formyl, acetyl, etc.), aralkyl (e.g. trityl, etc.), lower alkoxy carbonyl (e.g. tert-pentyloxycarbonyl, etc.), substituted lower alkanoyl, substituted lower alkoxycarbonyl, substituted or unsubstituted ar(lower-)alkoxycarbonyl, lower cycloalkoxycarbonyl, substituted phenylthio, substituted alkylidene, substituted aralkylidene, substituted cycloalkylidene or the like. Suitable acid to be used in this acidic hydrolysis may include an organic or inorganic acid such as formic acid, trifluoroacetic acid, benzenesulfonic acid, p-toluenesulfonic acid, hydrochloric acid, cation-exchange resin, and the like. Preferable acid is the one which can easily be separated out from the reaction product by a conventional manner such as neutralization or distillation under reduced pressure, for example, formic acid, trifluoroacetic acid, hydrochloric acid or the like. The acid suitable for the reaction can be selected in consideration of the chemical property of the starting compound and the product as well as the kind of the protective group to be eliminated. The acidic hydrolysis can be conducted in the presence or absence of a solvent. Suitable solvent may be a conventional organic solvent, water or a mixture thereof which does not adversely influence this reaction. The hydrolysis using trifluoroacetic acid is accelerated by addition of anisole.

The basic hydrolysis can be preferably, applied for eliminating the protective group such as an acyl group, for example, haloalkanoyl (e.g. trifluoroacetyl, etc.) and the like. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as alkali metal acetate (e.g. sodium acetate, potassium acetate, etc.), trialkylamine (e.g. trimethylamine, triethylamine, etc.), picoline, N-methylpyrrolidine, N-methylmorpholine, 1,5-diazabicyclo[4,3,0]-5-nonene, 1,4-diazabicyclo[2,2,2]-octane, 1,5-diazabicyclo[5,4,0]-7-undecene, anion-exchange resin or the like. The hydrolysis using a base is often carried out in water or a conventional organic solvent or a mixture thereof.

The hydrolysis using hydrazine can be applied for eliminating the protective group such as dibasic acyl, for example, succinyl, phthaloyl or the like.

The reduction can be applied for eliminating the protective group such as acyl, for example, halo(lower)-alkoxycarbonyl (e.g. trichloroethoxycarbonyl, etc.), substituted or unsubstituted ar(lower)alkoxycarbonyl (e.g. benzyloxycarbonyl, p-nitrobenzyloxycarbonyl, etc.), 2-pyridylmethoxycarbonyl, etc., ar(lower)alkyl (e.g. benzyl, benzhydryl, trityl, etc.) and the like. Suitable reduction may include, for example, reduction using an alkali metal borohydride (e.g. sodium borohydride, etc.), conventional catalytic hydrogenolysis and the like.

And further, the protective group such as halo(-lower)alkoxycarbonyl, or 8-quinolyloxycarbonyl can be eliminated by treatment with a heavy metal such as copper, zinc or the like.

The reaction temperature is not critical and may be optionally selected in consideration of the chemical property of the starting compound and reaction product as well as the kind of the N-protective group and the method to be applied, and the reaction is preferably carried out under a mild condition such as under cooling, at ambient temperature or slightly elevated temperature.

The process includes in its scope the cases that the amino-protective groups of the protected amino(lower-)alkyl moiety in $R^2$ and $R^3$ are eliminated and/or that the protected carboxy for $R^4$ is simultaneously transformed into the free carboxy group in the course of the above reaction or in the post-treatment.

As to this process, it is to be understood that the purpose of this process lies in providing the generally more active compound ($I_c$) by eliminating the protective group in the protected amino group of the compound ($I_{c'}$) prepared by the other processes as mentioned above or below.

Process D

Elimination of amino-protective group in $R_a^3$

A compound ($I_d$) or its salt can be prepared by subjecting a compound ($I_{d'}$) or its salt to elimination reaction of the protective group in the protected amino(lower)alkyl moiety for $R_a^3$.

The elimination reaction can be conducted in the same manner as the above Process C.

This process includes in its scope the cases that the amino-protective groups of the protected amino for $R^1$ and protected amino(lower)alkyl for $R^2$ are eliminated and/or that the protected carboxy for $R^4$ is simultaneously transformed into the free carboxy group in the course of the above reaction or the post-treatment.

Process E

Elimination of hydroxy-protective group

A compound ($I_e$) or its salt can be prepared by subjecting a compound ($I_{e'}$) or its salt to elimination reaction of the protective group of the protected hydroxy(lower)alkyl for $R_a^2$.

This reaction may be conducted in a similar manner to that of the aforementioned Process C.

This process includes in its scope the cases that the amino-protective group of the protected amino for $R^1$ and/or the protected amino(lower)alkyl moiety in $R^2$ and $R^3$ are eliminated in the course of the reaction or post-treatment.

The compound obtained in accordance with the processes as explained above can be isolated and purified in a conventional manner.

In case that the object compound (I) has free amino for $R^1$, free amino(lower)alkyl-substituted heterocyclic group for $R^3$ and/or free carboxy for $R^4$, it may be transformed into its pharmaceutically acceptable salt by a conventional method.

Process F:

Elimination of amino-protective group in $R_c^2$

A compound ($I_f$) or its salt can be prepared by subjecting a compound ($I_{f'}$), or its salt to elimination reaction of the protective group in the protected amino(lower)alkyl for $R_c^2$.

The elimination reaction can be conducted in the same manner as the above Process C.

This process includes in its scope, the cases that amino-protective group of the protected amino for $R^1$ and/or the protected amino moiety in $R^3$ is eliminated, and/or the protected carboxy for $R^4$ is simultaneously transformed into the free carboxy group in the course of the above reaction or the post-treatment.

Process G:

Carboxy formation in $R_e^2$

A compound ($I_g$) or its salt can be prepared by subjecting a compound ($I_{g'}$) or its salt to a reaction of transforming an esterified carboxy moiety into carboxy moiety.

The reaction is carried out by conventional method, such as hydrolysis, reduction or the like.

The hydrolysis can be conducted in the same manner as the above Process C. The reduction may be conducted with a conventional reducing agent which is used for transforming the esterified carboxy group to a free carboxy group, for example, an alkali metal borohydride (e.g., sodium borohydride etc.), palladium carbon, palladium oxide, platinum oxide, and the like.

The reaction temperature is not critical and may be suitable selected in accordance with the kind of the ester and the method to be applied, and the present reaction is preferably carried out under a mild condition such as under cooling, at ambient temperature or slightly elevated temperature.

Process H:

Carboxy formation

A compound ($I_h$) or its salt can be prepared by subjecting a compound ($I_{h'}$) or its salt to elimination reaction of the protective group at the carboxy for $R_a^4$.

The elimination reaction of this process can be conducted in the same manner as the above Process G.

The compound obtained in accordance with the processes as explained above can be isolated and purified in a conventional manner.

In case that the object compound (I) has free amino for $R^1$, free amino(lower)alkyl for $R^2$, free amino(lower)alkyl-substituted heterocyclic group for $R^3$ and/or free carboxy for $R^4$, it may be transformed into its pharmaceutically acceptable salt by a conventional method.

The object compound (I) and its pharmaceutically acceptable salt exhibit high antimicrobial activities inhibiting the growth of a wide variety of pathogenic microorganisms including Gram-positive and Gram-negative bacteria and are useful as antimicrobial agents.

In order to show the utility of the compound (I) the test data of some representative compounds (I) are shown in the following.

1. In vitro antibacterial activity:

(1) Test method:

In vitro antibacterial activity was determined by the two-fold agar-plate dilution method as described below.

One loopful of an overnight culture of each test strain in Trypticase soy broth was streaked on heart infusion agar (HI-agar) containing graded concentration of the test compound and incubated at 37° C. for 20 hours. The minimal inhibitory concentration (MIC) was expressed in μg/ml.

(2) Test compound:

No.1 7-[2-(2-aminothiazol-4-yl)-2-(3-aminopropoxyimino)acetamido]-3-(5-aminomethyl-1,3,4-thiadiazol-2-yl)thiomethyl-3-cephem-4-carboxylic acid trihydrochloride (syn isomer)

No.2 7-[2-(2-aminothiazol-4-yl)-2-(2-aminoethoxyimino)acetamido]-3-[1-(2-aminoethyl)-1H-tetrazol-5-yl]thiomethyl-3-cephem-4-carboxylic acid trihydrochloride (syn isomer)

No.3 7-[2-(2-aminothiazol-4-yl)-2-carboxymethoxyiminoacetamido]-3-[1-(2-aminoethyl)-1H-tetrazol-5-ylthiomethyl]-3-cephem-4-carboxylic acid (syn isomer)

No.4 7-[2-(2-aminothiazol-4-yl)-2-(2-hydroxyethoxyimino)acetamido]-3-[1-(2-hydroxyethyl)-1H-tetrazol-5-ylthiomethyl]-3-cephem-4-carboxylic acid hydrochloride (syn isomer)

No.5 7-[2-(2-aminothiazol-4-yl)-2-propargyloxyiminoacetamido]-3-[1-(2-hydroxyethyl)-1H-tetrazol-5-ylthiomethyl]-3-cephem-4-carboxylic acid (syn isomer)

(3) Test results:

MIC (μg/ml)

| Test strains | Compound No. | | | | |
|---|---|---|---|---|---|
| | 1 | 2 | 3 | 4 | 5 |
| Escherichia coli NIHJ JC-2 | 0.200 | 0.390 | 0.100 | 0.200 | 0.390 |

-continued

| Test strains | Compound No. | | | | |
|---|---|---|---|---|---|
| | 1 | 2 | 3 | 4 | 5 |
| Klebsiella pneumoniae 20 | 0.200 | 0.100 | 0.100 | 0.050 | 0.100 |
| Proteus vulgaris 2 | 1.560 | 1.560 | 0.050 | 0.050 | 0.050 |
| Serratia marcescens 35 | 100.00 | 3.130 | 12.500 | 25.000 | 50.000 |
| Enterobacter eloacae 60 | 6.250 | 1.560 | 12.500 | 25.000 | 50.000 |
| Enterobacter aerogenes 20 | 6.250 | 0.390 | 6.250 | 12.500 | 6.250 |

For prophylactic and/or therapeutic administration, the compound (I) of the present invention is used in the form of conventional pharmaceutical preparation which contains said compound, as an active ingredient, in admixture with pharmaceutically acceptable carriers such as an organic or inorganic solid or liquid excipient which is suitable for oral, parenteral or external administration. The pharmaceutical preparations may be in solid form such as capsule, tablet, dragee, ointment or suppository, or in liquid form such as solution, suspension, or emulsion. If needed, there may be included in the above preparations auxiliary substances, stabilizing agents, wetting or emulsifying agents, buffers and the other commonly used additives.

While the dosage of the compounds may vary from and also depend upon the age and conditions of the patient, a kind of disease and a degree of the infection, and further a kind of the active compound (I) to be applied, etc., an average single dose of about 50 mg., 100 mg., 250 mg. and 500 mg. of the active compound (I) is sufficient for treating infectious diseases caused by pathogenic bacteria. In general, the active compound (I) can be administered in an amount between 1 mg/kg and 100 mg/kg, preferably 5 mg/kg and 50 mg/kg.

Following preparations and examples are given only for explanation of this invention in more detail.

Preparation 1

(1) Allyl bromide (2.91 g) was added dropwise to a stirred suspension of ethyl 2-(2-tritylaminothiazol-4-yl)-2-hydroxyiminoacetate (syn isomer, 10 g), N,N-dimethylformamide (100 ml) and potassium carbonate (4.54 g) under ice cooling over 5 minutes, and stirred at the same temperature for 4 hours. After adding water (200 ml) to the resultant solution, the solution was extracted with diethyl ether twice. The extract was washed with a saturated aqueous solution of sodium chloride and dried over magnesium sulfate. The solution was concentrated in vacuo, and the residue was triturated with a solution of n-hexane and diethyl ether. The precipitates were collected by filtration to give ethyl 2-(2-tritylaminothiazol-4-yl)-2-allyloxyiminoacetate (syn isomer, 9.4 g), mp. 130° to 132° C.

I.R. $\nu_{max}^{Nujol}$: 3380, 1735, 1520, 1550 cm$^{-1}$

N.M.R. δ(DMSO-d$_6$, ppm): 1.08 (3H, t, J=7 Hz), 3.96 (2H, q, J=7 Hz), 4.54 (2H, broad d, J=5 Hz), 5.0-5.5 (2H, m), 5.6-6.3 (1H, m), 6.90 (15H, broad s), 7.74 (1H, s)

(2) A solution of ethyl 2-(2-tritylaminothiazol-4-yl)-2-allyloxyiminoacetate (syn isomer, 8.7 g), 50% formic acid (42.5 ml) and tetrahydrofuran (42.5 ml) was stirred at 60° C. for 40 minutes. After concentrating the resultant solution in vacuo, the residue was dissolved in ethyl acetate, washed with an aqueous solution of sodium bicarbonate and a saturated aqueous solution of sodium chloride in turn, and dried over magnesium sulfate. After concentrating the resultant solution in vacuo, the residue was subjected to column chromatography on silica gel with benzene and ethyl acetate in turn, to give ethyl 2-(2-aminothiazol-4-yl)-2-allyloxyiminoacetate (syn isomer, 3.7 g), mp. 102° to 104° C.

I.R. $\nu_{max}^{Nujol}$: 3460, 3260, 3130, 1725, 1620, 1540, 1460 cm$^{-1}$

N.M.R. δ(DMSO-d$_6$, ppm): 1.25 (3H, t, J=7 Hz), 4.30 (2H, q, J=7 Hz), 4.61 (2H, d,d, J=5 Hz, 1 Hz), 5.0-5.5 (2H, m), 5.6-6.5 (1H, m), 6.95 (1H, s), 7.28 (2H, s)

(3) A solution of ethyl 2-(2-aminothiazol-4-yl)-2-allyloxyiminoacetate (syn isomer, 3.6 g), 2 N aqueous solution of sodium hydroxide (14.1 ml), tetrahydrofuran (14.1 ml) and methanol (15 ml) was stirred at 40° C. for 1.5 hours. The resultant solution was concentrated in vacuo, and the residue was dissolved in water. After the solution was adjusted to pH 2.8 with 10% hydrochloric acid under ice cooling, the precipitates were collected by filtration, washed with water and acetone in turn and dried to give 2-(2-aminothiazol-4-yl)-2-allyloxyiminoacetic acid (syn isomer, 1.91 g), mp. 187° C. (dec.).

I.R. $\nu_{max}^{Nujol}$: 3350, 1630, 1580, 1460 cm$^{-1}$

N.M.R. δ(DMSO-d$_6$, ppm): 4.61 (2H, d, J=6 Hz), 5.1-5.5 (2H, m), 5.7-6.2 (1H, m), 6.84 (1H, s), 7.25 (2H, broad s)

Preparation 2

(1) A mixture of ethyl 2-hydroxyimino-3-oxobutyrate (syn isomer, 56.7 g), N,N-dimethylformamide (280 ml), potassium carbonate (72.3 g) and propargyl bromide (43 g) was stirred at room temperature for 4 hrs. The reaction mixture was treated in a conventional manner to give ethyl 2-propargyloxyimino-3-oxobutyrate (syn isomer, 71.2 g).

I.R. $\nu_{max}^{Film}$: 3280, 3220, 2120, 1735, 1670 cm$^{-1}$ (2) A mixture of ethyl 2-propargyloxyimino-3-oxobutyrate (syn isomer, 71.2 g), acetic acid (81 ml) and sulfuryl chloride (50.2 g) was stirred at 40° C. for 10 minutes and then at room temperature for 5.5 hrs. The reaction mixture was treated in a conventional manner to give ethyl 4-chloro-3-oxo-2-propargyloxyiminobutyrate (syn isomer, 61.6 g.), oil.

I.R. $\nu_{max}^{Film}$: 3300, 2130, 1745, 1720, 1675 cm$^{-1}$

N.M.R. δ(CCl$_4$, ppm): 1.39 (3H, t, J=7 Hz), 2.57 (1H, t, J=2 Hz), 4.36 (2H, q, J=7 Hz), 4.56 (2H, s), 4.86 (2H, d, J=2 Hz)

(3) A mixture of ethyl 4-chloro-3-oxo-2-propargyloxyiminobutyrate (syn isomer, 61 g), thiourea (20 g), sodium acetate 3-hydrate (35.8 g), water (150 ml), and ethanol (180 ml) was stirred at 40° C. for 1.25 hrs. The reaction mixture was treated in a conventional manner to give ethyl 2-(2-aminothiazol-4-yl)-2-propargyloxyiminoacetate (syn isomer, 35.6 g).

I.R. $\nu_{max}^{Nujol}$: 3290, 2220, 1729 cm$^{-1}$

N.M.R. δ(DMSO-d$_6$, ppm): 1.28 (3H, t, J=7 Hz), 3.49 (1H, t, J=3 Hz), 4.31 (2H, q, J=7 Hz), 4.76 (2H, d, J=3 Hz), 6.95 (1H, s), 7.29 (2H, s).

(4) A mixture of ethyl 2-(2-aminothiazol-4-yl)-2-propargyloxyiminoacetate (syn isomer, 2.8 g.), methanol (23 ml.), tetrahydrofuran (20 ml.) and 1 N aqueous solution of sodium hydroxide (22.17 ml.) was stirred at 30° C. for 5 hrs. The reaction mixture was treated in a conventional manner to give 2-(2-aminothiazol-4-yl)-2-propargyloxyiminoacetic acid (syn isomer, 1.924 g.).

I.R. $\nu_{max}^{Nujol}$: 2190, 1740 cm$^{-1}$

N.M.R. δ(DMSO-d$_6$, ppm): 3.47 (1H, t, J=1.5 Hz), 4.74 (2H, d, J=1.5 Hz), 6.90 (1H, s)

Preparation 3

(1) A mixture of ethyl 2-hydroxyimino-3-oxobutyrate (syn isomer, 15.7 g.), 2-bromoethyl benzoate (27.5 g.), potassium carbonate (20.7 g.), N,N-dimethylformamide (25 ml.) and ethyl acetate (25 ml.) was stirred at room temperature for 4 hrs. The reaction mixture was treated in a conventional manner to give ethyl 2-(2-benzoyloxyethoxyimino)-3-oxobutyrate (syn isomer, 28 g.).

(2) A solution of ethyl 2-(2-benzoyloxyethoxyimino)-3-oxobutyrate (syn isomer, 28 g.), sulfuryl chloride (13.5 g.) and acetic acid (30 ml.) was stirred at 40° C. for 10 minutes and at room temperature for 5.5 hrs. The reaction mixture was treated in a conventional manner to give ethyl 2-(2-benzoyloxyethoxyimino)-4-chloro-3-oxobutyrate (syn isomer, 29 g.).

(3) A mixture of ethyl 2-(2-benzoyloxyethoxyimino)-4-chloro-3-oxobutyrate (syn isomer, 29 g.), thiourea (7.76 g.), sodium acetate (8.37 g.), water (75 ml.) and ethanol was stirred at 40° C. for an hour. The reaction mixture was treated in a conventional manner to give ethyl 2-(2-aminothiazol-4-yl)-2-(2-benzoyloxyethoxyimino)acetate (syn isomer, 9 g.).

N.M.R. $\delta$(DMSO-d$_6$, ppm): 1.28 (3H, t, J=7 Hz), 4.34 (2H, q, J=7 Hz), 4.56 (4H, m), 6.44 (2H, broad s), 6.68 (1H, s), 7.68–7.34 (3H, m), 8.06 (2H, d,d, J=8 Hz, 2Hz)

(4) A solution of ethyl 2-(2-aminothiazol-4-yl)-2-(2-benzoyloxyethoxyimino)acetate (syn isomer, 8.5 g.) in a mixture of 1 N aqueous sodium hydroxide (35 ml.), methanol (40 ml.) and tetrahydrofuran (40 ml.) was stirred at 40° C. for 9 hrs. and at room temperature for 12 hrs. The reaction mixture was treated in a conventional manner to give 2-(2-aminothiazol-4-yl)-2-(2-hydroxyethoxyimino)acetic acid (syn isomer, 3.3 g.).

I.R. $\nu_{max}^{Nujol}$: 3350, 3075, 1680, 1620 cm$^{-1}$
N.M.R. $\delta$(DMSO-d$_6$, ppm): 3.64 (2H, t, J=5 Hz), 4.10 (2H, t, J=5 Hz), 6.84 (1H, s), 7.16 (2H, m)

(5) A solution of formic acid (1.6 g.) and acetic anhydride (3.6 g.) was stirred at 50° C. for an hour. After cooling, 2-(2-aminothiazol-4-yl)-2-(2-hydroxyethoxyimino)acetic acid (syn isomer, 1 g.) was added to the solution and stirred at room temperature for 3 hours. Diisopropyl ether was added to the resultant solution, and the precipitates were filtered out. The filtrate was concentrated in vacuo, and the residue was pulverized with diisopropyl ether. The precipitates were collected by filtration to give 2-(2-formamidothiazol-4-yl)-2-(2-formyloxyethoxyimino)acetic acid (syn isomer, 0.7 g.).

I.R. $\nu_{max}^{Nujol}$: 3200, 1710, 1690 cm$^{-1}$
N.M.R. $\delta$ (DMSO-d$_6$, ppm): 4.38 (4H, s), 7.58 (1H, s), 8.26 (1H, s), 8.54 (1H, s)

Preparation 4

(1) A mixture of chloromethylthiomethane (7.97 g.), powdered potassium iodide (15.1 g.) and acetone (79 ml.) was stirred at room temperature for an hour, the resulting mixture was filtered and washed with a small amount of acetone. The washings and the filtrate were combined and added to a stirred suspension of ethyl 2-(2-formamidothiazol-4-yl)-2-hydroxyiminoacetate (syn isomer, 17.5 g.) and powdered potassium carbonate (15.5 g.) in acetone (300 ml.). The mixture was stirred at room temperature for 3 hours, filtered and washed with acetone. The washings and the filtrate was combined and concentrated in vacuo. The residue was dissolved in ethyl acetate, washed with a saturated aqueous solution of sodium chloride twice, dried over magnesium sulfate and concentrated in vacuo. The oily residue was subjected to column chromatography on silica gel and eluted with chloroform to give ethyl 2-(2-formamidothiazol-4-yl)-2-methylthiomethoxyiminoacetate (syn isomer, 2.4 g.), mp. 130° to 131° C.

I.R. $\nu_{max}^{Nujol}$: 3160, 3125, 3050, 1740, 1695 cm$^{-1}$
N.M.R. $\delta$ (DMSO-d$_6$, ppm): 1.32 (3H, t, J=7 Hz), 2.22 (3H, s), 4.38 (2H, q, J=7 Hz), 5.33 (2H, s), 7.67 (1H, s), 8.56 (1H, s)

(2) A mixture of ethyl 2-(2-formamidothiazol-4-yl)-2-methylthiomethoxyiminoacetate (syn isomer, 2.4 g.), 1 N aqueous sodium hydroxide (23.8 ml.) and methanol (19.8 ml.) was stirred at 30° C. for 2.5 hours. The resultant solution was adjusted to pH 7 with 10% hydrochloric acid and methanol was distilled off in vacuo. The aqueous solution was adjusted to pH 1 with 10% hydrochloric acid under ice cooling, and extracted with ethyl acetate three times. The extracts were washed with a saturated aqueous solution of sodium chloride, dried over magnesium sulfate and concentrated in vacuo to give 2-(2-formamidothiazol-4-yl)-2-methylthiomethoxyiminoacetic acid (syn isomer, 1.13 g.), mp. 157° C. (dec.).

I.R. $\nu_{max}^{Nujol}$: 3210, 3160, 3075, 1700, 1555 cm$^{-1}$
N.M.R. $\delta$ (DMSO-d$_6$, ppm): 2.24 (3H, s), 5.31 (2H, s), 7.61 (1H, s), 8.57 (1H, s), 12.73 (1H, s)

Preparation 5

Hydrazine hydrate (13.2 g.) was added to a suspension of N-phthalimidoxyethylphthalimide (38.4 g.) in ethanol (400 ml.) at 65° c. and stirred at 65° to 70° C. for an hour. After adding conc. hydrochloric acid (28 ml.) and water (280 ml.) to the resultant solution under ice-cooling, the insoluble substance was filtered off. The filtrate was concentrated in vacuo, washed with ethyl acetate and adjusted to pH 7.0 with 10% sodium hydroxide solution. After washing the solution with ethyl acetate, ethanol (400 ml.) and 2-(2-formamidothiazol-4-yl)glyoxylic acid (16.0 g.) were added to the solution and stirred at room temperature at pH 4.5 to 4.8 for 2 hours. The solvent was removed in vacuo, and ethyl acetate was added to the residue. The solution was adjusted to pH 0.3 with conc. hydrochloric acid. The aqueous solution was separated and adjusted to pH 5.6 with 10% sodium hydroxide solution. To the solution were added dioxane (600 ml.), triethylamine (16.0 g.) and 2-tert-butoxycarbonyloxyimino-2-phenylacetaonitrile (23.6 g.), and stirred at room temperature overnight. After removing the solvent in vacuo, the residue was washed with ethyl acetate. The aqueous solution was separated and ethyl acetate was added thereto. The mixture was adjusted to pH 2.0 with 10% hydrochloric acid under ice-cooling. The organic layer was separated and washed with saturated aqueous sodium chloride solution. The solution was dried over magnesium sulfate and evaporated in vacuo. The residue was pulverized with diisopropyl ether to give 2-(2-formamidothiazol-4-yl)-2-(2-tert-butoxycarbonylaminoethoxyimino)acetic acid (syn isomer, 13.3 g.).

I.R. $\nu_{max}^{Nujol}$: 3140, 1698, 1604 cm$^{-1}$
N.M.R. $\delta$ (DMSO-d$_6$, ppm): 1.37 (9H, s), 3.20 (2H, m), 3.97 (2H, m), 7.33 (1H, s), 8.50 (1H, s)

Preparation 6

Trimethylsilylphosphite (8.0 g.) was added to a solution of 2-(2-formamidothiazol-4-yl)-2-(2-azidoethoxyimino)acetic acid (syn isomer, 3.4 g.) and bis(trimethylsilyl)acetamide (5.4 g.) in pyridine (20 ml.) and stirred at room temperature for 20 hours. Water (10 ml.)

was added to the resultant solution at 5° to 10° C. and evaporated to vacuo. Water and ethyl acetate were added to the residue and adjusted to pH 1.5 with 10% hydrochloric acid. The aqueous layer was separated and adjusted to pH 7.0 with 10% sodium hydroxide. Dioxane (30 ml.), triethylamine (6.0 g.) and 2-tert-butoxycarbonyloxyimino-2-phenylacetonitrile (4.9 g.) were added to the resultant solution, and stirred at room temperature for 15 hours. After removing the solvent in vacuo, ethyl acetate was added to the residue and adjusted to pH 6.0 with 10% hydrochloric acid under ice-cooling. The aqueous solution was separated and ethyl acetate was added thereto. The mixture was adjusted to pH 2.0 with 10% hydrochloric acid under ice-cooling. The ethyl acetate layer was separated, washed with saturated sodium chloride solution and dried over magnesium sulfate. The solution was concentrated in vacuo and the residue was pulverized with diisopropyl ether to give 2-(2-formamidothiazol-4-yl)-2-(2-tert-butoxycarbonylaminoethoxyimino)acetic acid (syn isomer, 1.7 g.).

I.R. $\nu_{max}^{Nujol}$: 3140, 1698, 1604 cm$^{-1}$

Preparation 7

100% Hydrazine hydrate (10.0 g.), N-phthaliminoxypropylphthalimide (35 g.), 2-(2-formamidothiazol-4-yl)glyoxylic acid (8.86 g.) and 2-tert-butoxycarbonyloxyimino-2-phenylacetonitrile (29.6 g.) were treated in a similar manner to that of Example 5 to give 2-(2-formamidothiazol-4-yl)-2-(3-tert-butoxycarbonylaminopropoxyimino)acetic acid (syn isomer, 6.0 g.).

I.R. $\nu_{max}^{Nujol}$: 3360, 3170, 1700, 1570, 1540 cm$^{-1}$

N.M.R. δ (DMSO-d$_6$, ppm): 1.40 (9H, s), 1.80 (2H, m), 3.07 (2H, m), 4.18 (2H, t, J=7 Hz), 7.57 (1H, s), 8.57 (1H, s), 12.7 (1H, broad s)

Preparation 8

(1) A solution of N-(3-aminopropyl)acetamide (146 g) in dioxane (710 ml) was added to a solution of 97% sodium hyroxide (52 g) in water (620 ml) and then carbon disulfide (96 g) was added dropwise thereto over 35 minutes at −1° to 3° C. The mixture was stirred for 1 hour at 0° to 2° C. To the mixture containing sodium N-(3-acetamidopropyl)dithiocarbamate was added dropwise methyl iodide (179 g) over 35 minutes at 0° to 5° C. and then the resulting mixture was stirred for 3 hours at the same temperature. Dioxane was distilled off in vacuo from the reaction mixture and the residue was extracted with ethyl acetate (300 ml, 200 ml×4). The extracts were dried over magnesium sulfate and concentrated in vacuo to give oil of methyl N-(3-acetamidopropyl)dithiocarbamate (193.18 g).

(2) A mixture of a solution of methyl N-(3-acetamidopropyl)dithiocarbamate (193 g) in dioxane (610 ml) and a solution of sodium azide (79.42 g) in water (500 ml) was refluxed under stirring for 4 hours. Dioxane was distilled off and the remaining aqueous layer was washed with diethyl ether (150 ml×2), adjusted to pH 1 with 17.5% hydrochloric acid, and cooled in an ice bath. Precipitates were collected by filtration and washed with ice-water to give white powder of 1-(3-acetamidopropyl)-1H-tetrazol-5-thiol (91.75 g), mp. 152° to 154° C.

N.M.R. (d$_6$-DMSO) δ: 1.87 (3H, s), 1.97 (2H, m), 3.17 (2H, m), 4.28 (2H, t, J=7 Hz), 7.9 (1H, broad s), 15.0 (1H, broad s)

(3) A mixture of 1-(3-acetamidopropyl)-1H-tetrazole-5-thiol (85 g) and 6 N hydrochloric acid (1 l) was refluxed for 75 minutes under stirring. The reaction mixture was concentrated in vacuo and precipitates were collected by filtration and washed with hexane and diethyl ether to give 1-(3-aminopropyl)-1H-tetrazole-5-thiol hydrochloride (67.15 g).

N.M.R. (D$_2$O) δ: 2.45 (2H, m), 3.23 (2H, t, J=7 Hz), 4.50 (2H, t, J=7 Hz)

(4) A solution of 2-t-butoxycarbonyloxyimino-2-phenylacetonitrile (12.3 g) in dioxane (30 ml) was added under ice-cooling to a stirred solution of 1-(3-aminopropyl)-1H-tetrazole-5-thiol hydrochloride (9.78 g) and triethylamine (11.1 g) in a mixture of dioxane (25 ml) and water (25 ml), and then the resulting mixture was stirred for 1.75 hours at ambient temperature. Dioxane was distilled off and to the residue were added diethyl ether and a small amount of water. After shaking, the aqueous layer was separated and the organic layer was extracted twice with 10% potassium carbonate. The extracts combined with the separated aqueous layer were washed three times with diethyl ether, adjusted to pH 1 with hydrochloric acid and extracted with diethyl ether. The extract was washed with water, dried and evaporated in vacuo. The residue oil (10.92 g) was pulverized with diisopropyl ether to give 1-[3-(N-t-butoxycarbonylamino)propyl]-1H-tetrazole-5-thiol (9.6 g), mp. 75° to 77° C.

I.R. (Nujol): 3380, 3260, 1650, 1530, 1170, 1050 cm$^{-1}$

N.M.R. (CDCl$_3$) δ: 1.50 (9H, s), 2.14 (2H, m), 3.25 (2H, m), 4.39 (2H, t, J=7 Hz), 4.9–6.7 (1H, broad)

Preparation 9

The following compounds were obtained in any of a similar manner to those of Preparation 3.

(1) Ethyl 2-cyclopentyloxyimino-3-oxobutyrate (syn isomer), oil

I.R. $\nu_{max}^{Film}$: 1740, 1670, 1495, 1430 cm$^{-1}$

N.M.R. δ(CCl$_4$, ppm): 1.32 (3H, t, J=7 Hz), 1.4–2.2 (8H, m), 2.33 (3H, s), 4.27 (2H, q, J=7 Hz), 4.87 (1H, m)

(2) Ethyl 4-chloro-2-cyclopentyloxyimino-3-oxobutyrate (syn isomer), oil

I.R. $\vartheta_{max}^{Film}$: 1735, 1750, 1465, 1435 cm$^{-1}$

N.M.R. δ(CCl$_4$, ppm): 1.33 (3H, t, J=7 Hz), 1.3–2.4 (8H, m), 4.28 (2H, q, J=7 Hz) 4.46 (2H, s), 4.86 (1H, s)

(3) Ethyl 2-(2-aminothiazol-4-yl)-2-cyclopentyloxyiminoacetate (syn isomer), mp. 134°–136° C.

I.R. $\nu_{max}^{Nujol}$: 3490, 3450, 3250, 3120, 1735, 1540, 1460 cm$^{-1}$

N.M.R. δ(DMSO-d$_6$): 1.25 (3H, t, J=7 Hz), 1.62 (8H, broad s), 4.27 (2H, q, J=7 Hz), 4.70 (1H, m), 6.85 (1H, s), 7.20 (2H, s).

(4) 2-(2-Aminothiazol-4-yl)-2-cyclopentyloxyiminoacetic acid (syn isomer), mp. 186° C. (dec.).

I.R. $\nu_{max}^{Nujol}$: 3330, 3120, 1635, 1450 cm$^{-1}$

N.M.R. δ(DMSO-d$_6$): 1.1–2.2 (8H, m), 4.68 (1H, m), 6.81 (1H, s), 7.18 (2H, broad s).

(5) 2-[2-(2,2,2-trifluoroacetamido)thiazol-4-yl]-3-cyclopentyloxyiminoacetic acid (syn isomer).

I.R. $\nu_{max}^{Nujol}$: 3200, 3130, 1720, 1590, 1580 cm$^{-1}$

N.M.R. δ(DMSO-d$_6$): 1.34–2.22 (8H, m), 4.81 (1H, m), 7.71 (1H, s)

(6) To acetic anhydride (32 g.) was added formic acid (14.4 g.) under ice-cooling and stirred at 40° to 45° C. for an hour. 2-(2-Aminothiazol-4-yl)-2-cyclopentyloxyiminoacetic acid (syn isomer, 20 g.) and tetrahydrofuran (100 ml.) were added to the solution under ice-cooling and stirred at 35° C. for 3 hours. After the solution was concentrated in vacuo, the residue was pulverized with diisopropyl ether, and dried over phosphorus pentoxide to give 2-(2-formamidothiazol-4-yl)-2-cyclopentyloxyiminoacetic acid (syn isomer, 9.04 g.), mp. 158° C. (dec.).

I.R. $\nu_{max}^{Nujol}$: 3100, 1730, 1695, 1685, 1550, 1495 cm$^{-1}$

N.M.R. δ(DMSO-d$_6$): 1.2–2.3 (8H, m), 4.77 (1H, quintet, J=4 Hz), 7.93 (1H, s), 9.37 (1H, s).

EXAMPLE 1

(1) A solution of 2-(2-formamidothiazol-4-yl)-2-methoxyiminoacetic acid (syn isomer, 1.4 g) in dry ethyl acetate (20 ml) was added to a mixture of dry dimethylformamide (0.5 g), dry ethyl acetate (2.0 ml) and phosphoryl chloride (1.0 g) to give an activated acid solution. On the other hand, 7-amino-3-[1-(2-hydroxyethyl)-1H-tetrazol-5-ylthiomethyl]-3-cephem-4-carboxylic acid (2.0 g) and trimethylsilylacetamide (5.9 g) were added to dry ethyl acetate (40 ml), stirred at 40° C. and cooled to −10° C. To the solution was added the activated acid solution at −5° to −10° C. and stirred at the same temperature for an hour. Water (40 ml) was added to the reaction mixture and adjusted to pH 7.0 with sodium bicarbonate. The aqueous layer was separated and washed with ethyl acetate and diethyl ether successively. After removing the remaining ethyl acetate and diethyl ether by bubbling with nitrogen gas, the aqueous solution was adjusted to pH 2.0 with conc. hydrochloric acid and stirred for 30 minutes. The precipitates were collected by filtration, washed with chilled water and then dried over phosphorus pentoxide to give 7-[2-(2-formamidothiazol-4-yl)-2-methoxyiminoacetamido]-3-[1-(2-hydroxyethyl-1H-tetrazol-5-ylthiomethyl]-3-cephem-4-carboxylic acid (syn isomer, 2.10 g).

I.R. (Nujol) ν max: 1760, 1660 cm$^{-1}$

N.M.R. (DMSO-d$_6$) δ ppm: 3.46–4.04 (4H, m), 3.90 (3H, s), 4.12–4.53 (4H, m), 5.12 (1H, d, J=5.0 Hz), 5.79 (1H, d,d, J=5.0 Hz, 8.0 Hz), 7.42 (1H, s), 8.52 (1H, s), 9.67 (1H, d, J=8.0 Hz)

(2) A mixture of 7-[2-(2-formamidothiazol-4-yl)-2-methoxyiminoacetamido]-3-[1-(2-hydroxyethyl 1H-tetrazol-5-ylthiomethyl]-3-cephem-4-carboxylic acid (syn isomer, 2.0 g), conc.hydrochloric acid (0.73 g) and methanol (14.0 ml) was stirred at room temperature for 3 hrs. and evaporated in vacuo. The residue was dissolved in aqueous solution of sodium bicarbonate and then acidified to pH 3 with 10% hydrochloric acid. The precipitates were collected, washed with chilled water and dried over phosphorus pentoxide to give 7-[2-(2-aminothiazol-4-yl)-2-methoxyiminoacetamido]-3-[1-(2-hydroxyethyl-1H-tetrazol-5-ylthiomethyl]-3-cephem-4-carboxylic acid (syn isomer, 1.1 g)

I.R. (Nujol) ν max: 3350, 1775, 1670, 1635 cm$^{-1}$

N.M.R. (DMSO-d$_6$) δ ppm: 3.33–4.10 (4H, m), 3.83 (3H, s), 4.10–4.61 (4H, m), 5.11 (1H, d, J=4.3 Hz), 5.77 (1H, d,d, J=4.3 Hz, 8.0 Hz), 6.76 (1H, s), 9.60 (1H, d, J=8.0 Hz)

EXAMPLE 2

(1) A solution of 7-amino-3-[1-(2-hydroxyethyl-1H-tetrazol-5-ylthiomethyl]-3-cephem-4-carboxylic acid (2.0 g) and trimethylsilylacetamide (5.9 g) in dry ethyl acetate (40.0 ml) and a solution of 2-(2-formamidothiazol-4-yl)-2-allyloxyiminoacetic acid (syn isomer, 1.6 g), dry dimethylformamide (0.5 g) and phosphoryl chloride (1.0 g) in dry ethyl acetate 22.0 ml were treated in a similar manner to that of Example 1-(1) to give 7-[2-(2-formamidothiazol-4-yl)-2-allyloxyiminoacetamido]-3-[1-(2-hydroxyethyl)-1H-tetrazol-5-ylthiomethyl]-3-cephem-4-carboxylic acid (syn isomer, 2.79 g).

I.R. (Nujol) νmax: 3180, 1770, 1665 cm$^{-1}$

N.M.R. (DMSO-d$_6$) δppm: 3.48–3.95 (4H, m), 4.03–4.50 (4H, m), 4.50–4.78 (2H, m), 5.01–5.54 (3H, m), 5.65–6.60 (2H, m), 7.41 (1H, s), 8.53 (1H, s), 9.67 (1H, d, J=8.5 Hz)

(2) 7-[2-(2-Formamidothiazol-4-yl)-2-allyloxyiminoacetamido]-3-[1-(2-hydroxyethyl)-1H-tetrazol-5-ylthiomethyl]-3-cephem-4-carboxylic acid (syn isomer, 2.7 g) was treated with conc. hydrochloric acid (0.94 g) in a similar manner to that of Example 1-(2) to give 7-[2-(2-aminothiazol-4-yl)-2-allyloxyiminoacetamido]-3-[1-(2-hydroxyethyl)-1H tetrazol-5-ylthiomethyl]-3-cephem-4-carboxylic acid hydrochloride (syn isomer, 2.72 g).

I.R. (Nujol) νmax: 3340, 3210, 1772, 1730, 1665 cm$^{-1}$

N.M.R. (DMSO-d$_6$) δppm: 3.44–3.83 (4H, m), 4.00–4.40 (4H, m), 4.57 (2H, m), 4.95–5.47 (3H, m), 5.53–6.74 (4H, m), 6.82 (1H, s), 9.77 (1H, d, J=8.0 Hz)

EXAMPLE 3

(1) A solution of 7-amino-3-[1-(2-hydroxyethyl) 1H-tetrazol-5-ylthiomethyl]-3-cephem-4-carboxylic acid (2.0 g) and trimethylsilylacetamide (5.9 g) in dry ethyl acetate (40.0 ml) and a solution of 2-(2-formamidothiazol-4-yl)-2-propargyloxyiminoacetic acid (syn isomer, 1.6 g), dry dimethylformamide (0.5 g) and phosphoryl chloride (1.0 g) in dry ethyl acetate (52.0 ml) were treated in a similar manner to that of Example 1-(1) to give 7-[2-(2-formamidothiazol-4-yl)-2-propargyloxyiminoacetamido]-3-[1-(2-hydroxyethyl)-1H-tetrazol-5-ylthiomethyl]-3-cephem-4-carboxylic acid (syn isomer, 2.00 g).

I.R. (Nujol) νmax: 3260, 1780, 1670 cm$^{-1}$

N.M.R. (DMSO-d$_6$) δppm: 3.49 (1H, m), 3.57–4.05 (4H, m), 4.09–4.67 (4H, m), 4.79 (2H, m), 5.15 (1H, d, J=5.0 Hz), 5.81 (1H, d,d, J=5.0 Hz, 8.0 Hz), 7.46 (1H, s), 8.55 (1H, s), 9.76 (1H, d, J=8.0 Hz)

(2) 7-[2-(2-Formamidothiazol-4-yl)-2-propargyloxyiminoacetamido]-3-[1-(2-hydroxyethyl)-1H-tetrazol-5-ylthiomethyl]-3-cephem-4-carboxylic acid (syn isomer, 1.9 g) was treated with conc. hydrochloric acid (0.67 g) in a similar manner to that of Example 1-(2) to give 7-[2-(2-aminothiazol-4-yl)-2-propargyloxyiminoacetamido]-3-[1-(2-hydroxyethyl)-1H-tetrazol-5-ylthiomethyl]-3-cephem-4-carboxylic acid (syn isomer, 1.19 g).

I.R. (Nujol) νmax: 3300, 1775, 1670 cm$^{-1}$

N.M.R. (DMSO-d$_6$) δppm: 3.47 (1H, m), 3.56–4.00 (4H, m), 4.00–4.56 (4H, m), 4.72 (2H, m), 5.14 (1H, d, J=5.0 Hz), 5.79 (1H, d,d, J=5.0 Hz, 8.0 Hz), 6.82 (1H, s), 9.67 (1H, d, J=8.0 Hz).

EXAMPLE 4

(1) A solution of 7-amino-3-[1-(2-hydroxyethyl)-1H-tetrazol-5-ylthiomethyl]-3-cephem-4-carboxylic acid (2.16 g) in 50% aqueous acetone (22 ml) and a solution of 2-(2-formamidothiazol-4-yl)-2-methylthiomethoxyiminoacetic acid (syn isomer, 1.5 g), dimethylformamide (0.48 g) and phosphoryl chloride (1.01 g) in tetrahydrofuran (15 ml) were treated in a similar manner to that of Example 1-(1) to give 7-[2-(2-formamidothiazol-4-yl)-2-methylthiomethoxyiminoacetamido]-3-[1-(2-hydroxyethyl)-1H-tetrazol-5-ylthiomethyl]-3-cephem-4-carboxylic acid (syn isomer, 2.58 g).

I.R. (Nujol) νmax: 3420, 3250, 3050, 1770, 1660, 1540 cm$^{-1}$

N.M.R. (DMSO-d$_6$) δppm: 2.23 (3H, s), 3.52–3.97 (4H, m), 4.11–4.62 (4H, m), 5.17 (1H, d, J=5 Hz), 5.28

(2H, s), 5.85 (1H, d,d, J=5 Hz, 8 Hz), 7.47 (1H, s), 8.54 (1H, s), 9.75 (1H, d, J=8 Hz), 12.69 (1H, broad s)

(2) 7-[2-(2-Formamidothiazol-4-yl)-2-methylthiomethoxyiminoacetamido]-3-[1-(2-hydroxyethyl)-1H tetrazol-5-ylthiomethyl]-3-cephem-4-carboxylic acid (syn isomer, 2.5 g) was treated with conc. hydrochloric acid (0.88 g) in a similar manner to that of Example 1-(2) to give 7-[2-(2-aminothiazol-4-yl)-2-methylthiomethoxyiminoacetamido]-3-[1-(2-hydroxyethyl)-1H-tetrazol-5-ylthiomethyl]-3-cephem-4-carboxylic acid (syn isomer, 1.8 g).

I.R. (Nujol) $\nu$max: 3350, 1780, 1670, 1630, 1540 cm$^{-1}$

N.M.R. (DMSO-d$_6$) $\delta$ppm: 2.16 (3H, s), 3.3–3.9 (4H, m), 4.0–4.6 (4H, m), 5.08 (1H, d, J=5 Hz), 5.15 (2H, s), 5.76 (1H, d, d, J=5 Hz, 8 Hz), 6.76 (1H, s), 7.22 (2H, broad s), 9.77 (1H, d, J=8 Hz)

EXAMPLE 5

(1) A solution of 7-amino-3-[1-(2-hydroxyethyl)-1H-tetrazol-5-ylthiomethyl]-3-cephem-4-carboxylic acid (2.0 g) and trimethylsilylacetamide (5.9 g) in dry ethyl acetate (40 ml) and a solution of 2-(2-formamidothiazol-4-yl)-2-(2-formyloxyethoxyimino)acetic acid (syn isomer, 1.8 g), dry dimethylformamide (0.5 g) and phosphoryl chloride, (1.0 g) in dry ethyl acetate (22.0 ml) were treated in a similar manner to that of Example 1-(1) to give 7-[2-(2-formamidothiazol-4-yl)-2-(2-formyloxyethoxyimino)acetamido]-3-[1-(2-hydroxyethyl)-1H-tetrazol 5-ylthiomethyl]-3-cephem-4-carboxylic acid (syn isomer, 1.10 g).

I.R. (Nujol) $\nu$max: 3170, 1770, 1660 cm$^{-1}$

N.M.R. (DMSO-d$_6$) $\delta$ppm: 3.43–3.88 (4H, m), 3.95–4.60 (8H, m), 5.11 (1H, d, J=5.0 Hz), 5.79 (1H, d,d, J=5.0 Hz, 8.0 Hz), 7.42 (1H, s), 8.22 (1H, s), 8.51 (1H, s), 9.65 (1H, d, J=8.0 Hz)

(2) 7-[2-(2-Formamidothiazol-4-yl)-2-(2-formyloxyethoxyiminoacetamido]-3-[1-(2-hydroxyethyl)-1H-tetrazol-5-ylthiomethyl]-3-cephem-4-carboxylic acid (syn isomer, 1.0 g) was treated with conc. hydrochloric acid (0.66 g) in a similar manner to that of Example 1-(2) to give 7-[2-(2-aminothiazol 4-yl)-2-(2-hydroxyethoxyimino)acetamido]-3-[1-(2-hydroxyethyl)-1H-tetrazol-5-ylthiomethyl]-3-cephem 4-carboxylic acid (syn isomer, 0.97 g).

I.R. (KBr) $\nu$max: 3300, 3100, 2970, 1770, 1735, 1640 cm$^{-1}$

N.M.R. (DMSO-d$_6$) $\delta$ppm: 3.50–3.95 (6H, m), 4.00–4.63 (6H, m), 5.14 (1H, d, J=5.0 Hz), 5.28–6.85 (3H, m), 6.93 (1H, s) 9.71 (1H, d, J=8.0 Hz)

EXAMPLE 6

(1) Vilsmeier reagent was prepared from N,N-dimethyl-formamide (0.65 g.) and phosphoryl chloride (1.4 g.) in a usual manner. 2-(2-Formamidothiazol-4-yl)-2-(3-tert-butoxycarbonylaminopropoxyimino)acetic acid (syn isomer, 3.0 g.) was added to a stirred suspension of the Vilsmeier reagent in ethyl acetate (30 ml.) under ice-cooling and stirred at the same temperature for 30 minutes [Solution A]. Trimethylsilylacetamide (8.1 g.) was added to a stirred suspension of 7-amino-3-(5-tert-butoxycarbonylaminomethyl-1,3,4-thiadiazol-2-yl)thiomethyl-3-cephem-4-carboxylic acid (3.7 g.) in ethyl acetate (40 ml.) and stirred at room temperature for 30 minutes. The solution A was added to the solution all at once at −30° C., and stirred at −10° to −40° C. for an hour. Water and ethyl acetate (100 ml.) were added to the resultant mixture at −10° C., and the ethyl acetate layer was separated. Water (100 ml.) was added to the ethyl acetate layer and adjusted to pH 7.0 with saturated aqueous sodium bicarbonate solution. The aqueous layer was separated. Ethyl acetate was added to the solution and adjusted to pH 3.8 with 10% hydrochloric acid under ice-cooling. The ethyl acetate layer was separated and washed with saturated sodium chloride solution. The solution was dried over magnesium sulfate and concentrated in vacuo. The residue was pulverized with diisopropyl ether to give 7-[2-(2-formamidothiazol-4-yl)-2-(3-tert-butoxycarbonylaminopropoxyimino)acetamido]-3-(5-tert-butoxycarbonylaminomethyl-1,3,4-thiadiazol-2-yl)thiomethyl-3-cephem-4-carboxylic acid (syn isomer, 1.6 g.).

I.R. $\nu_{max}$Nujol: 3400–3200, 1780, 1690, 1530 cm$^{-1}$

N.M.R. $\delta$(DMSO-d$_6$, ppm): 1.42 (9H, s), 1.80 (2H, m), 3.70 (2H, m), 3.73 (2H, broad s), 4.00–4.87 (6H, m), 5.20 (1H, d, J=5 Hz), 5.87 (1H, dd, J=5 Hz, 8 Hz), 7.10 (1H, s), 8.55 (1H, s), 9.67 (1H, d, J=8 Hz)

(2) A mixture of 7-[2-(2-formamidothiazol-4-yl)-2-(3-tert-butoxycarbonylaminopropoxyimino)acetamido]-3-(5-tert-butoxycarbonylaminomethyl-1,3,4-thiadiazol-2-yl)thiomethyl-3-cephem-4-carboxylic acid (syn isomer, 1.5 g.), conc. hydrochloric acid (0.8 ml.), methanol (30 ml.) and tetrahydrofuran (30 ml.) was stirred at room temperature for 3 hours. After evaporation, methanol was added to the residue. The solution was evaporated in vacuo again, and the residue was dissolved in water (30 ml.). The solution was adjusted to pH 3.5 with saturated aqueous sodium bicarbonate solution under ice-cooling. The solution was subjected to column chromatography on macroporous non-ionic adsorption resin "Diaion HP-20" (trademark: Mitsubishi Chemical Industries Ltd.) and eluted with 30% aqueous isopropyl alcohol. The eluate was concentrated in vacuo and lyophilized to give 7-[2-(2-aminothiazol-4-yl)-2-(3-aminopropoxyimino)acetamido]-3-(5-aminomethyl-1,3,4-thiadiazol-2-yl)thiomethyl-3-cephem-4-carboxylic acid (syn isomer, 0.6 g.).

I.R. $\nu_{max}$Nujol: 3400–3100, 1770, 1660, 1610, 1530 cm$^{-1}$

N.M.R. $\delta$(DMSO-d$_6$, ppm): 2.03 (2H, m), 3.00 (2H, m), 3.70 (2H, m), 3.93–4.83 (6H, m), 5.13 (1H, d, J=5 Hz), 5.77 (1H, dd, J=5 Hz, 8 Hz), 6.78 (1H, s), 9.62 (1H, d, J=8 Hz)

EXAMPLE 7

(1) 2-(2-Formamidothiazol-4-yl)-2-(3-tert-butoxycarbonylaminopropoxyimino)acetic acid (syn isomer, 2.6 g.), N,N-dimethylformamide (0.6 g.), phosphoryl chloride (1.2 g.), 7-amino-3-[1-(2-tert-butoxycarbonylaminoethyl)-1H-tetrazol-5-yl]thiomethyl-3-cephem-4-carboxylic acid (3.2 g.), trimethylsilylacetamide (5.5 g.) and ethyl acetate (65 ml.) were treated in a similar manner to that of Example 6-(1) to give 7-[2-(2-formamidothiazol-4-yl) -2-(3-tert-butoxycarbonylaminopropoxyimino)acetamido]-3-[1-(2-tert-butoxycarbonylaminoethyl)-1H-tetrazol-5-yl]thiomethyl-3-cephem-4-carboxylic acid (syn isomer, 1.3 g.).

I.R. $\nu_{max}$Nujol: 3350, 3200, 1780, 1690, 1650, 1540 cm$^{-1}$

N.M.R. $\delta$(DMSO-d$_6$, ppm): 1.40 (18H, s), 1.83 (2H, m), 3.08 (2H, m), 3.20–3.66 (2H, m), 3.77 (2H, broad s), 3.92–4.73 (6H, m), 5.20 (1H, d, J=5 Hz), 5.88 (1H, dd, J=5 Hz, 8 Hz), 7.45 (1H, s), 8.58 (1H, s), 9.67 (1H, d, J=8 Hz), 12.72 (1H, broad s)

(2) 7-[2-(2-Formamidothiazol-4-yl)-2-(3-tert-butoxycarbonylaminopropoxyimino)acetamido]-3-[1-(2-tert-butoxycarbonylaminoethyl)-1H-tetrazol-5-yl]thiomethyl-3-cephem-4-carboxylic acid (syn isomer, 2.8 g.), conc. hydrochloric acid (1.6 ml.) and methanol (60 ml.) were treated in a similar manner to that of Example 6-(2) to give 7-[2-(2-aminothiazol-4-yl)-2-(3-aminopropoxyimino)acetamido]-3-[1-(2-aminoethyl)-1H-tetrazol-5-yl]thiomethyl-3-cephem-4-carboxylic acid (syn isomer, 1.1 g.).

I.R. $\nu_{max}$Nujol: 3500–3100, 1770, 1660, 1640–1560, 1540 cm$^{-1}$

N.M.R. δ(DMSO-d$_6$, ppm): 2.00 (2H, m), 2.97 (2H, m), 3.17–4.17 (4H, m), 4.17–4.93 (6H, m), 5.08 (1H, d, J=5 Hz), 5.75 (1H, m), 6.77 (1H, s), 9.55 (1H, m)

EXAMPLE 8

(1) 2-(2-Formamidothiazol-4-yl)-2-(2-tert-butoxycarbonylaminoethoxyimino)acetic acid (syn isomer, 2 g.), N,N-dimethylformamide (0.45 g), phosphoryl chloride (1.03 g.), 7-amino-3-[1-(2-tert-butoxycarbonylaminoethyl)-1H-tetrazol-5-yl]thiomethyl-3-cephem-4-carboxylic acid (2.6 g.), trimethylsilylacetamide (5.9 g.) and ethyl acetate (50 ml.) were treated in a similar manner to that of Example 6-(1) to give 7-[2-(2-formamidothiazol-4-yl)-2-(2-tert-butoxycarbonylaminoethoxyimino)acetamido]-3-[1-(2-tert-butoxycarbonylaminoethyl)-1H-tetrazol-5-yl]thiomethyl-3-cephem-4-carboxylic acid (syn isomer, 3.7 g.).

I.R. $\nu_{max}$Nujol: 3300, 1780, 1680, 1540 cm$^{-1}$

N.M.R. δ(DMSO-d$_6$, ppm): 1.37 (18H, s), 3.07–3.60 (4H, m), 3.75 (2H, broad s), 3.93–4.57 (4H, m), 5.20 (1H, d, J=5 Hs), 5.90 (1H, dd, J=8 Hz, 5 Hz), 7.47 (1H, s), 8.57 (1H, s), 9.62 (1H, d, J=8 Hz), 12.72 (1H, broad s)

(2) Conc. hydrochloric acid (3.2 g.) was added to a solution of 7-[2-(2-formamidothiazol-4-yl)-2-(2-tert-butoxycarbonylaminoethoxyimino)acetamido]-3-[1-(2-tert-butoxycarbonylaminoethyl)-1H-tetrazol-5-yl]thiomethyl-3-cephem-4-carboxylic acid (syn isomer, 3.5 g.) in methanol (50 ml.) and stirred at room temperature for 2 hours. After removing the solvent in vacuo, methanol was added to the residue. The mixture was concentrated in vacuo again. The precipitates were collected by filtration and washed with diethyl ether to give 7-[2-(2-aminothiazol-4-yl)-2-(2-aminoethoxyimino)acetamido]-3-[1-(2-aminoethyl)-1H-tetrazol-5-yl]thiomethyl-3-cephem-4-carboxylic acid trihydrochloride (syn isomer, 2.8 g.)

I.R. $\nu_{max}$Nujol: 3500–3100, 1770, 1700, 1670, 1620, 1560, 1540 cm$^{-1}$

N.M.R. δ(DMSO-d$_6$, ppm): 3.0–3.53 (4H, m), 3.80 (2H, m), 4.17–4.83 (6H, m), 5.20 (1H, d, J=5 Hz), 5.80 (1H, dd, J=8 Hz, 5 Hz), 7.10 (1H, s), 9.93 (1H, d, J=8 Hz)

EXAMPLE 9

(1) 2-(2-Formamidothiazol-4-yl)-2-(2-tert-butoxycarbonylaminoethoxyimino)acetic acid (syn isomer, 2 g.), N,N-dimethylformamide (0.45 g.), phosphoryl chloride (1.03 g.), 7-amino-3-(5-tert-butoxycarbonylaminomethyl 1,3,4-thiadiazol-2-yl)thiomethyl-3-cephem-4-carboxylic acid (2.6 g.), trimethylsilylacetamide (5.9 g.) and bis(trimethylsilyl)acetamide (3.4 g.) and ethyl acetate (50 ml.) were treated in a similar manner to that of Example 6-(1) to give 7-[2-(2-formamidothiazol-4-yl)-2-(2-tert-butoxycarbonylaminoethoxyimino)acetamido]-3-(5-tert-butoxycarbonylaminomethyl-1,3,4-thiadiazol-2-yl)thiomethyl-3-cephem-4-carboxylic acid (syn isomer, 4.0 g.).

I.R. $\nu_{max}$Nujol: 3400, 3200, 1775, 1680, 1535 cm$^{-1}$

N.M.R. δ(DMSO-d$_6$, ppm): 3.12–3.43 (2H, m), 3.60 (2H, m), 4.03 (2H, m), 4.37 (2H, q, J=13 Hz), 4.17–4.57 (2H, m), 5.08 (1H, d, J=5 Hz), 5.57 (1H, dd, J=8 Hz, 5 Hz), 7.30 (1H, s), 8.40 (1H, s), 9.43 (1H, d, J=8 Hz), 12.55 (1H, broad s)

(2) 7-[2-(2-Formamidothiazol-4-yl)-2-(2-tert-butoxycarbonylaminoethoxyimino)acetamido]-3-(5-tert-butoxycarbonylaminomethyl-1,3,4-thiadiazol-2-yl)thiomethyl-3-cephem-4-carboxylic acid (syn isomer, 3.7 g.), conc. hydrochloric acid (2.9 g.) and methanol (50 ml.) were treated in a similar manner to that of Example 8-(2) to give 7-[2-(2-aminothiazol-4-yl)-2-(2-aminoethoxyimino)acetamido]-3-(5-aminomethyl-1,3,4-thiadiazol-2-yl)thiomethyl-3-cephem-4-carboxylic acid trihydrochloride (syn isomer, 2.9 g.).

I.R. $\nu_{max}$Nujol: 3500–3100, 1770, 1700, 1670, 1625, 1570, 1540 cm$^{-1}$

N.M.R. δ(DMSO-d$_6$, ppm): 3.30 (2H, m), 3.73 (2H, m), 4.10–4.80 (6H, m), 5.17 (1H, d, J=5 Hz), 5.77 (1H, dd, J=8 Hz, 5 Hz), 7.0 (1H, s), 9.90 (1H, d, J=8 Hz)

EXAMPLE 10

(1) Vilsmeier reagent was prepared from N,N-dimethylformamide (0.4 g.) and phosphoryl chloride (0.8 g.) in dry ethyl acetate (1.6 g.). Dry ethyl acetate (16 ml.) and 2-(2-formamidothiazol-4-yl)-2-(3-tert-butoxycarbonylaminopropoxyiminoacetic acid (syn isomer, 1.6 g.) were added to the Vilsmeier reagent [Solution A]. The solution A was added dropwise to a solution of 7-amino-3-(4-amino-5-methyl-4H-1,2,4-triazol-3-yl)thiomethyl-3-cephem-4-carboxylic acid (1.5 g.), and sodium bicarbonate (1.1 g.) in water (9 ml.) and acetone (9 ml.) at −2° to 3° C. while adjusting to pH 7.0 to 8.0 with triethylamine, and stirred at the same temperature for 30 minutes. Ethyl acetate and water were added to the resultant solution. The aqueous layer was separated and washed with ethyl acetate. The solution was concentrated in vacuo and the residue was adjusted to pH 2.5 with phosphoric acid under ice-cooling. The precipitates were collected by filtration, washed with water and dried over magnesium sulfate to give 7-[2-(2-formamidothiazol-4-yl)-2-(3-tert-butoxycarbonylaminopropoxyimino)acetamido]-3-(4-amino-5-methyl-4H-1,2,4-triazol-3-yl)thiomethyl-3-cephem-4-carboxylic acid (syn isomer, 1.55 g.).

I.R. $\nu_{max}^{Nujol}$: 1770, 1675 cm$^{-1}$

N.M.R. δ(DMSO-d$_6$, ppm): 1.39 (9H, s), 1.80 (2H, m), 2.31 (3H, s), 3.01 (2H, m), 3.67 (2H, m), 4.19 (4H, m), 5.13 (1H, d, J=4.0 Hz), 5.78 (1H, dd, J=4.0 Hz, 8.0 Hz), 7.41 (1H, s), 8.53 (1H, s), 9.62 (1H, d, J=8 Hz)

(2) A solution of 7-[2-(2-formamidothiazol-4-yl)-2-(3-tert-butoxycarbonylaminopropoxyimino)acetamido]-3-(4-amino-5-methyl-4H-1,2,4-triazol-3-yl)thiomethyl-3-cephem-4-carboxylic acid (syn isomer, 1.45 g.), and conc. hydrochloric acid (1.1 g.) in methanol (10.2 ml.) was treated in a similar manner to that of Example 8-(2) to give 7-[2-(2-aminothiazol-4-yl)-2-(3-aminopropoxyimino)acetamido]-3-(4-amino-5-methyl-4H-1,2,4-triazol-3-yl)thiomethyl-3-cephem-4-carboxylic acid trihydrochloride (syn isomer, 1.21 g.)

I.R. $\nu_{max}^{Nujol}$: 1780, 1670, 1630 cm$^{-1}$

N.M.R. δ(DMSO-d$_6$, ppm): 2.11 (2H, m), 2.90 (2H, m), 3.79 (2H, m), 4.04–4.75 (4H, m), 5.23 (1H, d, J=5.0 Hz), 5.82 (1H, dd, J=5.0 Hz, 9.0 Hz), 7.01 (1H, s), 9.94 (1H, d, J=9.0 Hz)

EXAMPLE 11

(1) 2-(2-Formamidothiazol-4-yl)-2-tert-butoxycarbonylmethoxyiminoacetic acid (syn isomer, 1.62 g.) was added to a solution of N,N-dimethylformamide (432 mg.) and phosphoryl chloride (905 mg.) in tetrahydrofuran (16 ml.) and treated in a similar manner to that of Example 6-(1). The solution was added to a solution of 7-amino-3-[1-(2-tert-butoxycarbonylaminoethyl)-1H-tetrazol-5-yl]thiomethyl-3-cephem-4-carboxylic acid (3.0 g.) and triethylamine in 50% aqueous acetone (30 ml.) at −5° to −3° C. and pH 7 to 7.5 and stirred for 30 minutes. Ethyl acetate was added to the resultant solution and adjusted to pH 2.0 with 10% hydrochloric acid. After removing the insoluble substance by filtration, water and ethyl acetate were added to the filtrate. The ethyl acetate layer was separated and washed with saturated sodium chloride solution. The solution was dried over magnesium sulfate and concentrated in vacuo. The residue was pulverized with diethyl ether and the precipitates were collected by filtration to give 7-[2-(2-formamidothiazol-4-yl)-2-tert-butoxycarbonylmethoxyiminoacetamido]-3-[1-(2-tert-butoxycarbonylaminoethyl)-1H-tetrazol-5-yl]thiomethyl-3-cephem-4-carboxylic acid (syn isomer, 2.93 g.).

I.R. $\nu_{max}^{Nujol}$: 3270, 1790, 1695, 1550, 1460 cm$^{-1}$

N.M.R. δ(DMSO-d$_6$, ppm): 1.28 (9H, s), 1.38 (9H, s), 3.27 (2H, broad s), 3.63 (2H, s), 4.24 (4H, s), 4.50 (2H, s), 5.04 (1H, d, J=5 Hz), 5.72 (1H, dd, J=5 Hz, 8 Hz), 8.36 (1H, s), 9.42 (1H, d, J=8 Hz), 12.52 (1H, s)

(2) A solution of 7-[2-(2-formamidothiazol-4-yl)-2-tert-butoxycarbonylmethoxyiminoacetamido]-3-[1-(2-tert-butoxycarbonylaminoethyl)-1H-tetrazol-5-yl]-thiomethyl-3-cephem-4-carboxylic acid (syn isomer, 3.5 g.) and conc. hydrochloric acid (1.9 g.) in methanol (35 ml.) was stirred at room temperature for 1.5 hours. After concentration, the residue was pulverized with diethyl ether to give 7-[2-(2-aminothiazol-4-yl)-2-tert-butoxycarbonylmethoxyiminoacetamido]-3-[1-(2-tert-butoxycarbonylaminoethyl)-1H-tetrazol-5-yl]thiomethyl-3-cephem-4-carboxylic acid hydrochloride (syn isomer, 3.32 g.).

I.R. $\nu_{max}^{Nujol}$: 3350 (broad), 1775, 1720, 1680, 1635, 1570, 1550 cm$^{-1}$ N.M.R. δ(DMSO-d$_6$, ppm): 1.42 (9H, s), 1.57 (9H, s), 3.36 (2H, broad s), 3.72 (2H, q, J=18 Hz), 4.32 (2H, s), 4.64 (4H, broad s), 5.15 (1H, d, J=5 Hz), 5.74 (1H, dd, J=5 Hz, 8 Hz), 7.02 (1H, s), 7.36 (2H, broad s), 9.75 (1H, d, J=8 Hz)

(3) Trifluoroacetic acid (12.8 ml.) was added portionwise to a chilled suspension of 7-[2-(2-aminothiazol-4-yl)-2-tert-butoxycarbonylmethoxyiminoacetamido]-3-[1-(2-tert-butoxycarbonylaminoethyl)-1H-tetrazol-5-yl]thiomethyl-3-cephem-4-carboxylic acid (syn isomer, 3.2 g.) in anisole (3.2 ml.), and stirred at room temperature for 70 minutes. After removing the solvent from the resultant mixture in vacuo, the residue was triturated with diethyl ether. The precipitates were collected by filtration, dried and dissolved in water (40 ml.). The solution was adjusted to pH 4.8 with 10% sodium hydroxide solution under ice-cooling. The solution was subjected to column chromatography on macroporous non-ionic adsorption resin "Diaion HP-20" (trademark: Mitsubishi Chemical Industries Ltd.) and eluted with 20% aqueous isopropyl alcohol. The eluate was concentrated in vacuo and lyophilized to give 7-[2-(2-aminothiazol-4-yl)-2-carboxymethoxyiminoacetamido]-3-[1-(2-aminoethyl)-1H-tetrazol-5-yl]thiomethyl-3-cephem-4-carboxylic acid (syn isomer, 1.2 g.).

I.R. $\nu_{max}^{Nujol}$: 3300, 3170, 1760, 1660, 1530 cm$^{-1}$

N.M.R. δ(DMSO-d$_6$, ppm): 3.44 (2H, broad s), 3.72 (2H, s), 3.9–5.2 (7H, m), 5.08 (1H, d, J=5 Hz), 5.73 (1H, broad s), 6.87 (1H, s), 7.22 (2H, broad s)

EXAMPLE 12

(1) 2-(2-Formamidothiazol-4-yl)-2-ethoxycarbonylmethoxyiminoacetic acid (syn isomer, 1.32 g.), N,N-dimethylformamide (447 mg.), phosphoryl chloride (939 mg.), 7-amino-3-[1-(2-tert-butoxycarbonylaminoethyl)-1H-tetrazol-5-yl]thiomethyl-3-cephem-4-carboxylic acid (3.0 g.), tetrahydrofuran (13 ml.) and 50% aqueous acetone (30 ml.) were treated in a similar manner to that of Example 11-(1) to give 7-[2-(2-formamidothiazol-4-yl)-2-ethoxycarbonylmethoxyiminoacetamido]-3-[1-(2-tert-butoxycarbonylaminoethyl)-1H-tetrazol-5-yl]-thiomethyl-3-cephem-4-carboxylic acid (syn isomer, 2.78 g.).

I.R. $\nu_{max}^{Nujol}$: 3260 (broad), 1780, 1690 (shoulder), 1540 cm$^{-1}$

N.M.R. δ(DMSO-d$_6$, ppm): 1.21 (3H, t, J=7 Hz), 3.37 (2H, broad s), 3.72 (2H, broad s), 4.16 (2H, q, J=7 Hz), 4.34 (4H, s), 4.73 (2H, s), 5.16 (1H, d, J=5 Hz), 5.85 (1H, dd, J=5 Hz, 8 Hz), 7.48 (1H, s), 8.58 (1H, s), 9.52 (1H, d, J=8 Hz), 12.24 (1H, s)

(2) 7-[2-(2-formamidothiazol-4-yl)-2-ethoxycarbonylmethoxyiminoacetamido]-3-[1-(2-tert-butoxycarbonylaminoethyl)-1H-tetrazol-5-yl]thiomethyl-3-cephem-4-carboxylic acid (syn isomer, 2.7 g.), conc. hydrochloric acid (1.52 g.) and ethanol (27 ml.) were treated in a similar manner to that of Example 11-(2) to give 7-[2-(2-aminothiazol-4-yl)-2-ethoxycarbonylmethoxyiminoacetamido]-3-[1-(2-aminoethyl)-1H-tetrazol-5-yl]-thiomethyl-3-cephem-4-carboxylic acid (syn isomer, 0.57 g.).

I.R. $\nu_{max}^{Nujol}$: 3300, 3170, 1760, 1670, 1530 cm$^{-1}$

N.M.R. δ(DMSO-d$_6$, ppm): 1.22 (3H, t, J=7 Hz), 3.42 (2H, broad s), 3.60 (2H, broad s), 4.16 (2H, q, J=7 Hz), 4.42 (2H, broad s), 5.07 (1H, d, J=5 Hz), 5.72 (1H, broad s), 6.80 (1H, s), 7.25 (2H, broad s), 9.48 (1H, broad s)

EXAMPLE 13

(1) 2-(2-Formamidothiazol-4-yl)-2-(2-tert-butoxycarbonylaminoethoxyimino)acetic acid (syn isomer, 2 g.), N,N-dimethylformamide (0.45 g.), phosphoryl chloride (1.0 g.), 7-amino-3-[1-(2-hydroxyethyl)-1H-tetrazol-5-yl]thiomethyl-3-cephem-4-carboxylic acid (2 g.), trimethylsilylacetamide (5.9 g.) and ethyl acetate (50 ml.) were treated in a similar manner to that of Example 6-(1) to give 7-[2-(2-formamidothiazol-4-yl)-2-(2-tert-butoxycarbonylaminoethoxyimino)acetamido]-3-[1-(2-hydroxyethyl)-1H-tetrazol-5-yl]thiomethyl-3-cephem-4-carboxylic acid (syn isomer, 2.7 g.).

I.R. $\nu_{max}^{Nujol}$: 3300, 1780, 1680, 1540 cm$^{-1}$

N.M.R. δ(DMSO-d$_6$, ppm): 1.35 (9H, s), 3.33 (2H, m), 3.75 (4H, m), 4.07 (2H, m), 4.33 (4H, m), 5.17 (1H, d, J=5 Hz), 5.87 (1H, dd, J=8 Hz, 5 Hz), 7.40 (1H, s), 8.50 (1H, s), 9.53 (1H, d, J=8 Hz), 12.57 (1H, m)

(2) 7-[2-(2-Formamidothiazol-4-yl)-2-(2-tert-butoxycarbonylaminoethoxyimino)acetamido]-3-[1-(2-hydroxyethyl)-1H-tetrazol-5-yl]thiomethyl-3-cephem-4-carboxylic acid (syn isomer, 2.5 g.), conc. hydrochloric acid (1.9 g.) and methanol (40 ml.) were treated in a similar manner to that of Example 6-(2) to give 7-[2-(2-aminothiazol-4-yl)-2-(2-aminoethoxyimino)acetamido]-3-[1-(2-hydroxyethyl)-1H-tetrazol-5-yl]thiomethyl-3-cephem-4-carboxylic acid (syn isomer, 1.4 g.).

I.R. $\nu_{max}^{Nujol}$: 3300, 3170, 1765, 1660, 1600, 1530 cm$^{-1}$

N.M.R. δ(DMSO-d$_6$, ppm): 3.13 (2H, m), 3.50 (2H, m), 3.73 (2H, m), 4.60–3.93 (6H, m), 4.97 (1H, d, J=5

Hz), 5.67 (1H, dd, J=8 Hz, 5 Hz), 6.75 (1H, s), 9.43 (1H, m)

EXAMPLE 14

(1) Vilsmeier reagent was prepared from N,N-dimethylformamide (0.53 g) and phosphoryl chloride (1.1 g) in a usual manner. 2-(2-Formamidothiazol-4-yl)-2-propargyloxyiminoacetic acid (syn isomer, 1.5 g) was added to a suspension of the Vilsmeier reagent in dry ethyl acetate (12 ml) under ice-cooling and stirred at the same temperature for 30 minutes [Solution A].

Trimethylsilylacetamide (4.72 g) was added to a stirred suspension of 7-amino-3-[1-(2-tert-butoxycarbonylaminoethyl)-(1H-tetrazol-5-yl)thiomethyl-3-cephem-4-carboxylic acid (3.05 g) in ethyl acetate (30 mg) and the mixture was stirred at room temperature for 30 minutes. To the solution was added the above [Solution A] all at once at −30° C. and stirred at −10° to −40° C. for an hour. Water and ethyl acetate were added to the reaction mixture at −10° C. The ethyl acetate layer was separated and extracted with an aqueous solution of sodium bicarbonate (pH 7.0). To the aqueous solution was added ethyl acetate and adjusted to pH 5.0 under ice-cooling. The ethyl acetate layer was separated, washed with a saturated aqueous solution of sodium chloride, dried over magnesium sulfate and concentrated in vacuo to give 7-[2-(2-formamidothiazol-4-yl)-2-propargyloxyiminoacetamido]-3-[1-(2-tert-butoxycarbonylaminoethyl)-1H-tetrazol-5-yl]thiomethyl-3-cephem-4-carboxylic acid (syn isomer, 1.16 g).

I.R. $\nu_{max}^{Nujol}$: 3275, 1780, 1690, 1540 cm$^{-1}$

N.M.R. δ(DMSO-d$_6$, ppm): 1.32 (9H, s), 3.03–3.58 (3H, m), 3.7 (2H, broad s), 4.18–4.5 (4H, m), 4.73 (2H, m), 5.13 (1H, d, J=5 Hz), 5.82 (1H, dd, J=5 Hz, 8 Hz), 7.43 (1H, s), 8.53 (1H, s), 9.78 (1H, d, J=8 Hz)

(2) A mixture of 7-[2-(2-formamidothiazol-4-yl)-2-propargyloxyiminoacetamido]-3-[1-(2-tert-butoxycarboxylaminoethyl)-1H-tetrazol-5-yl]thiomethyl-3-cephem-4-carboxylic acid (syn isomer, 0.63 g) and conc. hydrochloric acid (0.3 g) in methanol (5 ml) was stirred at 35° C. for 1.5 hours.

After evaporating the solvent from the resultant mixture, in vacuo, the residue was dissolved in methanol (10 ml). Methanol was added to the residue and evaporated in vacuo again. The residue was pulverized with diisopropyl ether to give 7-[2-(2-aminothiazol-4-yl)-2-propargyloxyiminoacetamido]-3-[1-(2-aminoethyl)-1H-tetrazol-5-yl]thiomethyl-3-cephem-4-carboxylic acid dihydrochloride (syn isomer, 0.52 g).

I.R. $\nu_{max}^{Nujol}$: 3300–3100, 1770, 1700(sh), 1670, 1630, 1540 cm$^{-1}$

N.M.R. δ(DMSO-d$_6$, ppm): 3.35 (2H, m), 3.55 (1H, m), 3.75 (2H, broad s), 5.05–4.15 (4H, m), 4.78 (2H, m), 5.13 (1H, d, J=5 Hz), 5.73 (1H, dd, J=5 Hz, 8 Hz), 6.93 (1H, s), 9.78 (1H, d, J=8 Hz).

EXAMPLE 15

(1) Vilsmeier reagent was prepared from N,N-dimethylformamide (0.6 g) and phosphoryl chloride (1.3 g) in dry ethyl acetate (2.4 ml) in a usual manner. Dry ethyl acetate (18 ml) and 2-(2-formamidothiazol-4-yl)-2-allyloxyiminoacetic acid (syn isomer, 1.8 g) were added to the solution of Vilsmeier reagent subsequently, and then stirred [Solution A].

Trimethylsilylacetamide (6.1 g) was added to a stirred suspension of 7-amino-3-[1-(2-tert-butoxycarbonylaminoethyl)-1H-tetrazol-5-yl]thiomethyl-3-cephem-4-carboxylic acid (3.0 g) in dry ethyl acetate (60 ml) and stirred at 40° C. for 30 minutes.

The solution A was added to the stirred solution at −5° to −10° C. and stirred at the same temperature for 30 minutes. After adding water to the resultant mixture, the insoluble substance was collected by filtration and dissolved in tetrahydrofuran. The ethyl acetate layer was separated from the filtrate and combined with the tetrahydrofuran solution. The solution was washed with a saturated sodium chloride solution and dried over magnesium sulfate. After concentrating the solution in vacuo, the residue was pulverized with diisopropyl ether, collected by filtration and washed with diisopropyl ether to give 7-[2-(2-formamidothiazol-4-yl)-2-allyloxyiminoacetamido]-3-[1-(2-tert-butoxycarbonylaminoethyl)-1H-tetrazol-5-yl]thiomethyl-3-cephem-4-carboxylic acid (syn isomer, 2.98 g).

I.R. $\nu_{max}^{Nujol}$: 1780, 1670 cm$^{-1}$

N.M.R. δ(DMSO-d$_6$, ppm): 1.35 (9H, s), 3.37 (2H, m), 3.67 (2H, m), 4.37 (4H, m), 4.66 (2H, m), 5.03–5.62 (3H, m), 5.67–6.34 (2H, m), 7.43 (1H, s), 8.54 (1H, s), 9.71 (1H, d, J=8.0 Hz)

(2) A suspension of 7-[2-(2-formamidothiazol-4-yl)-2-allyl-oxyiminoacetamido]-3-[1-(2-tert-butoxycarbonylaminoethyl)-1H-tetrazol-5-yl]thiomethyl-3-cephem-4-carboxylic acid (syn isomer, 2.9 g) and conc. hydrochloric acid (1.7 g) in methanol (20.3 ml) was stirred at room temperature for 2.7 hours. After removing the solvent in vacuo, methanol (20 ml) was added to the residue and evaporated in vacuo again. Water and ethyl acetate were added to the residue and adjusted to pH 7.5 with sodium bicarbonate. The aqueous solution was separated, washed with ethyl acetate and the remaining organic solvent was removed in vacuo. The aqueous solution was adjusted to pH 3.7 with 10% hydrochloric acid. The precipitates were collected by filtration, washed with water and dried over phosphorus pentoxide to give 7-[2-(2-aminothiazol-4-yl)-2-allyloxyiminoacetamido]-3-[1-(2-aminoethyl)-1H-tetrazol-5-yl]thiomethyl-3-cephem-4-carboxylic acid (syn isomer, 0.3 g). The mother liquid and the aqueous washing solution were combined together and subjected to column chromatography on macroporous nonionic adsorption resin "Diaion HP-20" [trademark: Mitsubishi Chemical Industries Ltd.] and eluted with 10% aqueous isopropyl alcohol. The eluate was concentrated in vacuo and lyophilized to give the same object compound (0.8 g). Total yield 1.1 g.

I.R. $\nu_{max}^{Nujol}$: 3270, 3150, 1760, 1660, 1610 cm$^{-1}$

N.M.R. δ(DMSO-d$_6$, ppm): 3.37 (2H, m), 3.60 (2H, m), 3.23 (2H, m), 4.30–4.91 (4H, m), 4.91–5.50 (3H, m), 5.50–6.43 (2H, m), 6.69 (1H, s), 7.17 (2H, broad s), 9.51 (1H, d, J=8.0 Hz)

EXAMPLE 16

(1) A mixture of 7-aminocephalosporanic acid (252.3 g.), 1-(3-tert-butoxycarbonylaminopropyl)-1H-tetrazole-5-thiol (240 g.), sodium bicarbonate (171 g.), water (6 l.) and acetone (1.5 l.) was stirred at 60° to 65° C. for 3 hours. The resultant mixture was cooled to 10° to 15° C. and adjusted to pH 4.0 with 10% hydrochloric acid. The precipitates were collected by filtration and washed with water and acetone in turn to give 7-amino-3-[1-(3-tert-butoxycarbonylaminopropyl)-1H-tetrazol-5-ylthiomethyl]-3-cephem-4-carboxylic acid (189.4 g.).

I.R. $\nu_{max}^{Nujol}$: 3350, 3150, 1800, 1700, 1620, 1540 cm$^{-1}$

N.M.R. δ(Dcl+D$_2$O, ppm): 1.25 (9H, s), 2.37 (2H, m), 3.23 (2H, m), 3.87 (2H, s), 4.37 (2H, s), 4.67 (2H, t. J=7 Hz), 5.18 (1H, d, J=5 Hz), 5.37 (1H, d, J=5 Hz)

(2) 2-(2-Formamidothiazol-4-yl)-2-tert-butoxycarbonylmethoxyiminoacetic acid (syn isomer, 16.5 g.), N,N-dimethylformamide (4.4 g.), phosphoryl chloride (9.2 g.), 7-amino-3-[1-(3-tert-butoxycarbonylaminopropyl)-1H-tetrazol-5-ylthiomethyl]-3-cephem-4-carboxylic acid (23.6 g.), sodium carbonate (5.3 g.), tetrahydrofuran (100 ml.), acetone (150 ml.) and water (150 ml.) were treated in a similar manner to that of Example 11-(1) to give 7-[2-(2-formamidothiazol-4-yl)-2-tert-butoxycarbonylmethoxyiminoacetamido]-3-[1-(3-tert-butoxycarbonylaminopropyl)-1H-tetrazol-5-ylthiomethyl]-3-cephem-4-carboxylic acid (syn isomer, 39.1 g.).

I.R. $\nu_{max}^{Nujol}$: 3250, 1780, 1680 (broad s), 1540 cm$^{-1}$

N.M.R. δ(DMSO-d$_6$, ppm): 1.40 (18H, s), 2.07 (2H, m), 2.97 (2H, m), 3.73 (2H, m), 4.37 (4H, m), 4.67 (2H, s), 5.22 (1H, d, J=5 Hz), 5.88 (1H, dd, J=8 Hz, 5 Hz), 7.50 (1H, s), 8.57 (1H, s), 9.62 (1H, d, J=8 Hz)

(3) Conc. hydrochloric acid (20.8 g.) was added to a mixture of 7-[2-(2-formamidothiazol-4-yl)-2-tert-butoxycarbonylmethoxyiminoacetamido]-3-[1-(3-tert-butoxycarbonylaminopropyl)-1H-tetrazol-5-ylthiomethyl]-3-cephem-4-carboxylic acid (syn isomer, 39.1 g.) in methanol (400 ml.), and stirred at room temperature for 4 hours. After removing the solvent in vacuo, tetrahydrofuran (40 ml.) and anisole (40 ml.) were added to the residue and stirred at room temperature for 4 hours. The reaction mixture was added to ethyl acetate at room temperature. The precipitates were collected by filtration and washed with ethyl acetate to give 7-[2-(2-aminothiazol-4-yl)-2-carboxymethoxyiminoacetamido]-3-[1-(3-aminopropyl)-1H-tetrazol-5-ylthiomethyl]-3-cephem-4-carboxylic acid (a mixture of syn and anti isomers). The product was subjected to column chromatography on macroporous nonionic absorption resin "HP-20" (trademark, manufactured by Mitsubishi Chemical Industries Co.) to give the syn isomer of the objective compound.

I.R. $\nu_{max}^{Nujol}$: 3300, 1760, 1660, 1600, 1520 cm$^{-1}$

N.M.R. (DMSO-d$_6$, ppm): 2.34 (2H, m), 3.16 (2H, m), 3.64 (2H, q, J=17 Hz), 4.24 (2H, q, J=13 Hz), 4.56–4.34 (4H, m), 5.20 (1H, d, J=5 Hz), 5.74 (1H, d, J=5 Hz), 7.04 (1H, s)

EXAMPLE 17

Sodium bicarbonate (0.5 g.) was dissolved in pH 6.8 phosphate buffer (30 ml.). 7-[2-(2-Aminothiazol-4-yl)-2-propargyloxyiminoacetamido]-cephalosporanic acid (syn isomer, 1.5 g.) and 1-(2-tert-butoxycarbonylaminoethyl)-1H-tetrazole-5-thiol (1.1 g.) were added to the solution at 60° to 65° C. and stirred at the same temperature for 3 hours. Ethyl acetate and tetrahydrofuran (2:1) were added to the resultant mixture and adjusted to pH 3.0 with 10% hydrochloric acid. The organic layer was separated and the aqueous layer was extracted with ethyl acetate. The ethyl acetate extract and the organic layer were combined together, washed with a saturated sodium chloride aqueous solution and dried over magnesium sulfate. After removing the solvent in vacuo, the residue was dissolved in methanol (30 ml.). After adding coc. hydrochloric acid (0.6 ml.) thereto, the mixture was repeatedly evaporated by adding methanol. The residue was pulverized with diethyl ether and collected by filtration to give 7-[2-(2-aminothiazol-4-yl)-2-propargyloxyiminoacetamido]-3-[1-(2-aminoethyl)-1H-tetrazol-5-ylthiomethyl]-3-cephem-4-carboxylic acid dihydrochloride (syn isomer, 0.3 g.)

I.R. $\nu_{max}^{Nujol}$: 3300, 3100, 1770, 1700 (sh), 1670, 1630, 1540 cm$^{-1}$ N.M.R. δ(DMSO-d$_6$, ppm): 3.35 (2H, m), 3.55 (1H, m), 3.75 (2H, broad s), 5.05–4.15 (4H, m), 4.78 (2H, m), 5.13 (1H, d, J=5 Hz), 5.73 (1H, dd, J=5 Hz, 8 Hz), 6.93 (1H, s), 9.78 (1H, d, J=8 Hz)

EXAMPLE 18

4-Amino-5-methyl-3-mercapto-4H-1,2,4-triazole (1.5 g.) was added to a stirred suspension of 7-[2-(2-aminothiazol-4-yl)-2-methoxyiminoacetamido]cephalosporanic acid (syn isomer, 3.7 g.) in 0.2 M phosphate buffer (30.0 ml.) at 65° C., and adjusted to pH 6.5 to 6.8. The solution was stirred at 65° C. for 5⅜ hours. The resultant mixture was adjusted to pH 5.0 with 10% hydrochloric acid and subjected to column chromatography on macroporous non-ionic adsorption resin "Diaion HP-20" (trademark: manufactured by Mitsubishi Chemical Industries Co.) with 10–20% aqueous isopropyl alcohol. The eluate was concentrated in vacuo and lyophilized to give 7-[2-(2-aminothiazol-4-yl)-2-methoxyiminoacetamido]-3-(4-amino-5-methyl-4H-1,2,4-triazol-3-ylthiomethyl)-3-cephem-4-4-carboxylic acid (syn isomer, 0.38 g.).

I.R. $\nu_{max}^{Nujol}$: 3350, 3250, 1770, 1670, 1600 cm$^{-1}$

N.M.R. (DMSO-d$_6$, ppm): 2.25 (3H, s), 3.45 (2H, m), 3.79 (3H, s), 4.15 (2H, m), 4.91 (1H, d, J=5 Hz), 5.53 (1H, dd, J=5 Hz, 8 Hz), 5.83 (2H, broad s), 6.69 (1H, s), 7.16 (2H, broad s), 9.72 (1H, d, J=8 Hz).

EXAMPLE 19

(1) 2-[2-(2,2,2-Trifluoroacetamido)thiazol-4-yl]-2-cyclopentyloxyiminoacetic acid (syn isomer, 1.5 g.), dry N, N-dimethylformamide (0.4 g.), phosphoryl chloride (0.8 g.), 7-amino-3-[1-(3-tert-butoxycarbonylaminopropyl)-1H-tetrazol-5-ylthiomethyl]-3-cephem-4-carboxylic acid (2.0 g.), sodium bicarbonate (1.4 g.), water (12.0 ml.), acetone (12.0 g.), and dry ethyl acetate (0.4 g.) were treated in a similar manner to that of Example 11-(1) to give 7-[2-[2-(2,2,2-trifluroacetamido)thiazol-4-yl]2-cyclopentyloxyiminoacetamido]-3-[1-(3-tert-butoxycarbonylaminopropyl)-1H-tetrazol-5-ylthiomethyl]-3-cephem-4-carboxylic acid (syn isomer, 2.60 g.).

I.R. $\nu_{max}^{Nujol}$: 3180, 1780, 1680 cm$^{-1}$

N.M.R. (DMSO-d$_6$, ppm): 1.25–2.26 (10H, m), 1.41 (9H, s), 2.97 (2H, m), 3.74 (2H, m), 4.06–4.57 (4H, m), 4.78 (1H, m), 5.21 (1H, d, J=4.0 Hz), 5.87 (1H, dd, J=4.0 Hz, 8.0 Hz), 7.53 (1H, s), 9.70 (1H, d, J=8.0 Hz).

(2) 7-[2-[2-(2,2,2-Trifuoroacetamido)thiazol-4-yl]-2-cyclopentyloxyiminoacetamido]-3-[1-(3-tert-butoxycarbonylaminopropyl)-1H-tetrazol-5-ylthiomethyl]-3-cephem-4-carboxylic acid (syn isomer, 2.5 g.) was dissolved in a solution of conc. hydrochloric acid (0.65 g.) in methanol (20 ml.).

After evaporating methanol in vacuo, the residue was dissolved in methanol (20 ml.) and evaporated in vacuo. Water (40 ml.) was added to the residue and adjusted to pH 2.0 with sodium bicarbonate. To the mixture were added sodium acetate tr hydrate (4.2 g.) and tetrahydrofuran (15 ml.), and stirred at room temperature overnight. The resultant solution was concentrated in vacuo, and adjusted to pH 3.8 with 1 N hydrochloric acid. The precipitates were collected by filtration, washed with water and dried over magnesium sulfate to give 7-[2-(2-aminothiazol-4-yl)-2-cyclopentyloxyiminoacetamido]-3-[1-(3-aminopropyl)-1H-tetrazol-5- ylthiomethyl]-3-cephem-4-carboxylic acid (syn isomer, 0.31 g.). The filtrate was subjected to column chromatography on non-ionic macroporous adsorption resin "Diaion-HP-20" [trademark: manufactured by Mitsubishi Chemical Industries Co.] with 15–20% aqueous isopropyl alcohol. The eluate was concentrated in vacuo and the residue was lyophilized to give the same object substance (0.62 g.) total yield (0.93 g.).

I.R. $\nu_{max}^{Nujol}$: 3270, 3160, 1760, 1610 cm$^{-1}$

N.M.R. (DMSO-d$_6$, ppm): 1.28–1.96 (8H, m), 2.16 (2H, m), 2.88 (2H, m), 3.54 (2H, m), 4.12–4.81 (5H, m), 5.02 (1H, d, J=5.0 Hz), 5.67 (1H, dd, J=5.0 Hz, 8.0 Hz), 6.67 (1H, s), 9.40 (1H, d, J=8.0 Hz)

EXAMPLE 20

(1) A solution of 2-[2-(2,2,2-trifluoroacetamido)-thiazol-4-yl]-2-cyclopentyloxyiminoacetic acid (syn isomer, 1.6 g.), dry N,N-dimethylformamide (0.4 g.), phosphoryl chloride (0.8 g.), dry ethyl acetate (1.6 ml.) and tetrahydrofuran (20 ml.), and a solution of 7-amino-3-[1-(2-hydroxyethyl)-1H-tetrazol-5-yl-thiomethyl]-3-cephem-4-carboxylic acid (1.5 g.), trimethylsilylacetamide (3.8 g.) and dry ethyl acetate (30 ml.) were treated in a similar manner to that of Example 1-(1) to give 7-[2-[2-(2,2,2-trifluoroacetamido)thiazol-4-yl]-2-cyclopentyloxyiminoacetamido]-3-[1-(2-hydroxyethyl)-1H-tetrazol-5-ylthiomethyl]-3-cephem-4-carboxylic acid (syn isomer, 2.63 g.).

I.R. (Nujol): 3200, 1770, 1710, 1660 cm$^{-1}$

N.M.R. (DMSO-d$_6$, ppm): 1.28–2.24 (8H, m), 3.39–4.04 (4H, m), 4.04–4.61 (4H, m), 4.80 (1H, m), 5.19 (1H, d, J=5.0 Hz), 5.86 (1H, dd, J=5.0 Hz, 8.0 Hz), 7.52 (1H, s), 9.68 (1H, d, J=8.0 Hz).

(2) A solution of 7-[2-[2-(2,2,2-trifluoroacetamido)-thiazol-4-yl]-2-cyclopentyloxyiminoacetamido]-3-[1-(2-hydroxyethyl)-1H-tetrazol-5-ylthiomethyl]-3-cephem-4-carboxylic acid (syn isomer, 2.5 g.), sodium acetate 3 hydrate (4.9 g.), water (30 ml.) and tetrahydrofuran (14.0 ml.) was stirred at room temperature for 18 hours. After removing tetrahydrofuran from the resultant solution in vacuo, water (20 ml.) was added to the residue and adjusted to pH 3.0 with 10% hydrochloric acid. The precipitates were collected by filtration, washed with water and dried over phosphorus pentoxide to give 7-[2-(2-aminothiazol-4-yl)-2-cyclopentyloxyiminoacetamido]-3-[1-(2-hydroxyethyl)-1H-tetrazol-5-ylthiomethyl]-3-cephem-4-carboxylic acid (syn isomer, 1.54 g.), mp. 150°–156° C. (dec.).

I.R. (Nujol): 3300, 3200, 1770, 1660, 1630 cm$^{-1}$

N.M.R. (DMSO-d$_6$, ppm): 1.19–2.09(8H, m), 3.36–3.99 (4H, m), 4.05–4.55 (4H, m), 4.67 (1H, m), 5.14 (1H, d, J=4.0 Hz), 5.80 (1H, dd, J=4.0 Hz, 8.0 Hz), 6.74 (1H, s), 9.51 (1H, d, J=8.0 Hz).

What we claim is:

1. A syn compound of the formula:

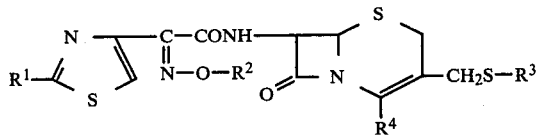

wherein
 $R^1$ is amino,
 $R^2$ is cyclopentyl,
 $R^3$ is hydroxy(lower)alkyltetrazolyl,
 and $R^4$ is carboxy,
and its pharmaceutically acceptable salt.

2. A compound of claim 1, which is 7-[2-(2-aminothiazol-4-yl)-2-cyclopentyloxyiminoacetamido]-3-[1-(2-hydroxyethyl)-1H-tetrazol-5-ylthiomethyl]-3-cephem-4-carboxylic acid (syn isomer).

3. A pharmaceutically antibacterial composition comprising a compound of claim 1 in association with a pharmaceutically acceptable, substantially non-toxic carrier or excipient.

* * * * *